US011195609B2

(12) United States Patent
Mustakos et al.

(10) Patent No.: US 11,195,609 B2
(45) Date of Patent: Dec. 7, 2021

(54) SYSTEMS AND METHODS FOR CLINICAL EFFECT-BASED NEUROSTIMULATION

(71) Applicant: Boston Scientific Neuromodulation Corporation, Valencia, CA (US)

(72) Inventors: Richard Mustakos, Simi Valley, CA (US); Tianhe Zhang, Studio City, CA (US); G. Karl Steinke, Valencia, CA (US); Stephen Carcieri, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 315 days.

(21) Appl. No.: 16/219,551

(22) Filed: Dec. 13, 2018

(65) Prior Publication Data

US 2019/0184171 A1 Jun. 20, 2019

Related U.S. Application Data

(60) Provisional application No. 62/598,558, filed on Dec. 14, 2017.

(51) Int. Cl.
*A61N 1/36* (2006.01)
*G16H 20/40* (2018.01)
(Continued)

(52) U.S. Cl.
CPC ......... *G16H 20/40* (2018.01); *A61N 1/36182* (2013.01); *G16H 40/00* (2018.01);
(Continued)

(58) Field of Classification Search
CPC . A61N 1/36103; A61N 1/36139; G16H 20/40
(Continued)

(56) References Cited

U.S. PATENT DOCUMENTS 5,941,251 A * 8/1999 Panescu .............. A61B 5/0066
128/899
8,340,758 B2 12/2012 Choi et al.
(Continued)

FOREIGN PATENT DOCUMENTS

WO WO-2014036075 A1 3/2014
WO WO-2019118667 A1 6/2019

OTHER PUBLICATIONS

Sudhyadhom, Atchar, et al., "A Three-dimensional Deformable Brain Atlas for DBS Targeting, I. Methodology for Atlas Creation and Artifact Reduction", The Open Neuroimaging Journal, 2012, 6, 92-98.
(Continued)

*Primary Examiner* — John R Downey
(74) *Attorney, Agent, or Firm* — Schwegman Lundberg & Woessner, P.A.

(57) ABSTRACT

This document discusses, among other things, systems and methods for delivering electrostimulation to specific tissue of a patient. An example of a system can receive a three-dimensional voxelized model representing a plurality of regions each specified as a target region or an avoidance region. The system includes control circuitry to determine a metric value using the voxelized model. The metric value indicates a clinical effect of electrostimulation on the plurality of regions according to a stimulation current and a current fractionalization. The control circuitry can determine a desired stimulation current that results in a first metric value satisfying a clinical effect condition. The system can generate a stimulation configuration including the desired stimulation current and the current fractionalization corresponding to the first metric value, and deliver tissue stimulation according to the stimulation configuration.

20 Claims, 13 Drawing Sheets

(51) Int. Cl.
*G16H 40/00* (2018.01)
*G16H 40/60* (2018.01)
*G16H 40/67* (2018.01)
*G16H 50/50* (2018.01)
*G16H 30/40* (2018.01)
*A61N 1/375* (2006.01)

(52) U.S. Cl.
CPC .......... *G16H 40/60* (2018.01); *A61N 1/3605* (2013.01); *A61N 1/36025* (2013.01); *A61N 1/36103* (2013.01); *A61N 1/36139* (2013.01); *A61N 1/36157* (2013.01); *A61N 1/37514* (2017.08); *G16H 30/40* (2018.01); *G16H 40/67* (2018.01); *G16H 50/50* (2018.01)

(58) Field of Classification Search
USPC ....................................................... 607/2–76
See application file for complete search history.

(56) References Cited

U.S. PATENT DOCUMENTS

| | | |
|---|---|---|
| 9,248,296 B2 | 2/2016 | Carcieri et al. |
| 9,457,188 B2 | 10/2016 | Kaemmerer |
| 9,561,380 B2 | 2/2017 | Carcieri et al. |
| 2013/0060305 A1* | 3/2013 | Bokil ................. A61N 1/36146 607/62 |
| 2014/0067018 A1* | 3/2014 | Carcieri ................. A61N 1/372 607/59 |
| 2015/0246233 A1* | 9/2015 | Kaemmerer ....... A61N 1/36139 607/59 |
| 2016/0067495 A1* | 3/2016 | Chaturvedi ........ A61N 1/36067 607/59 |
| 2016/0082262 A1 | 3/2016 | Parramon et al. |
| 2016/0144194 A1 | 5/2016 | Roothans et al. |
| 2016/0250476 A1* | 9/2016 | Kaemmerer ......... A61N 1/3614 607/45 |

OTHER PUBLICATIONS

"European Application Serial No. 18829688.3, Response filed Jan. 22, 2021 to Communication pursuant to Rules 161(1) and 162 EPC dated Jan. 22, 21", 8 pgs.

"International Application Serial No. PCT/US2018/065342, International Preliminary Report on Patentability dated Jun. 25, 2020", 7 pgs.

"International Application Serial No. PCT/US2018/065342, International Search Report dated Mar. 14, 2019", 4 pgs.

"International Application Serial No. PCT/US2018/065342, Written Opinion dated Mar. 14, 2019", 7 pgs.

"European Application Serial No. 18829688.3, Communication Pursuant to Article 94(3) EPC dated Apr. 6, 2021", 5 pgs.

* cited by examiner

SYSTEMS AND METHODS FOR CLINICAL EFFECT-BASED NEUROSTIMULATION

CLAIM OF PRIORITY

This application claims the benefit of priority under 35 U.S.C. § 119(e) of U.S. Provisional Patent Application Ser. No. 62/598,558, filed on Dec. 14, 2017, which is herein incorporated by reference in its entirety.

TECHNICAL FIELD

This document relates generally to medical devices and more particularly to a system for programming a stimulation device for neuromodulation using one or more clinical effects.

BACKGROUND

Neurostimulation, also referred to as neuromodulation, has been proposed as a therapy for a number of conditions. Examples of neurostimulanon include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

The neurostimulation energy may be delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of neurostimulation pulses. Some implantable neurostimulators have enhanced capabilities of providing multiple therapy modalities at various neural targets. The enhanced device functionality and expanded treatment space are accompanied by increased system complexity, both in the neurostimulators and the delivery system, such as leads and electrodes. For example, some implantable neurostitnulators can deliver stimulation using multiple directional leads with multiple longitudinal and circumferential electrodes and different therapy modes. Accordingly, complexity and time required for testing and programming stimulation electrodes and tuning stimulation parameters may increase substantially. Effectively and efficiently searching the sophisticated treatment space for a desirable and individualized electrostimulation therapy remains a technological challenge in computerized neurostimulation.

SUMMARY

An example (e.g., "Example 1") of a system for delivering neurostimulation to specific tissue of a patient and controlling the delivery of the neurostimulation by a user is provided. The system comprises a receiver circuit to receive a three-dimensional (3D) voxelized model of tissue representing a plurality of regions each specified as a target region or an avoidance region, and a control circuitry that includes a stimulation programmer circuit. The stimulation programmer circuit is configured to: determine a metric value using the 3D voxelized model, the metric value indicative of a clinical effect of electrostimulation on the plurality of regions according to a stimulation current and a current fractionalization across a plurality of electrodes; determine a first stimulation current that results in a first metric value satisfying a clinical effect condition, the first metric value associated with a corresponding electrode current fractionalization; and generate a stimulation configuration for tissue stimulation, the stimulation configuration including the first stimulation current and the current fractionalization corresponding to the first metric value.

In Example 2, the subject matter of Example 1 optionally includes an implantable stimulator and an external programming device communicatively coupled to the implantable stimulator. The implantable stimulator includes an electrostimulation generator circuit configured to generate stimulation energy for delivery to the tissue according to the generated stimulation configuration. The external programming device includes the receiver circuit and the control circuitry.

In Example 3, the subject matter of any one or more of Examples 1-2 optionally includes an image processor circuit coupled to the control circuitry. The receiver circuit may receive a 3D triangulated surface representation of the tissue, and the image processor circuit may transform the received 3D triangulated surface representation into the 3D voxelized model.

In Example 4, the subject matter of any one or more of Examples 1-3 optionally includes the stimulation programmer circuit that may generate the stimulation configuration, including searching for a desired stimulation location with respect to positions of the plurality of electrodes. The desired stimulation location may be represented by at least a longitudinal coordinate and an angular coordinate in a coordinate space, and correspond to the first metric value and its associated stimulation current.

In Example 5, the subject matter of Example 4 optionally includes the stimulation programmer circuit that may search for the longitudinal and angular coordinates that maximize the metric value.

In Example 6, the subject matter of Example 5 optionally includes the stimulation programmer circuit that may iteratively search for the longitudinal and angular coordinates using a gradient-based method. The stimulation programmer circuit may determine a metric gradient vector using a 3D triangulated surface spanned by three points in the coordinate space, and iteratively search for the longitudinal and angular coordinates using the metric gradient vector.

In Example 7, the subject matter of any one or more of Examples 1-6 optionally includes the 3D voxelized that may include 3D voxels each having a voxel volume. The stimulation programmer circuit may determine the first metric value for a stimulation location using a combination of the voxel volumes of the 3D voxels each weighted by a weight factor.

In Example 8, the subject matter of Example 7 optionally includes the weight factor correlative of a clinical effect of the stimulation on the target or avoidance region. The weight factor may be a positive scalar if the 3D voxel is situated in a target region, or a negative scalar if the voxel is situated in an avoidance region.

In Example 9, the subject matter of any one or more of Examples 7-8 optionally includes the stimulation programmer circuit that may determine, for the stimulation location, a lowest stimulation current that results in the first metric value under the current fractionalization.

In Example 10, the subject matter of Example 9 optionally includes the stimulation programmer circuit that may determine the lowest stimulation current using sorted 3D voxels in an ascending order of voxel current thresholds associated with the 3D voxels.

In Example 11, the subject matter of Example 9 optionally includes the stimulation programmer circuit that may determine the lowest stimulation current using amplitude bins arranged in an ascending order of amplitude ranges. The 3D voxels each may be assigned to one of the amplitude bins based on respective voxel current thresholds associated with the 3D voxels.

In Example 12, the subject matter of any one or more of Examples 1-11 optionally includes the stimulation configuration including a virtual electrode state. The virtual electrode state may include one or more virtual electrode steering parameters. The control circuitry may further include a virtual electrode control circuit to steer a virtual electrode on a graphical user interface according to the one or more virtual electrode steering parameters.

In Example 13, the subject matter of Example 12 optionally includes the virtual electrode that comprises a plurality of electrode primitives each having respective primitive voltage fields. The virtual electrode control circuit may construct a voltage field of the virtual electrode using superposition of the primitive voltage fields of the plurality of electrode primitives each scaled by respective weight factors.

In Example 14, the subject matter of Example 13 optionally includes a current fractionalization circuit that may convert the voltage field of the virtual electrode to a voltage field of the plurality of electrodes using regression fitting.

In Example 15, the subject matter of any one or more of Examples 13-14 optionally includes the virtual electrode control circuit that may estimate a threshold current using the voltage field of the virtual electrode. The threshold current is representative of a minimum current required for modulating a physiologic target.

Example 16 is a method for controlling delivery of electrostimulation to tissue via an external programming device. The method comprises steps of receiving a three-dimensional (3D) voxelized model of tissue via a receiver circuit, the 3D voxelized model representing a plurality of regions each specified as a target region or an avoidance region; and determining a metric value using the 3D voxelized model via a stimulation programmer circuit, the metric value indicative of a clinical effect of electrostimulation on the plurality of regions according to a stimulation current and a current fractionalization among the plurality of electrodes; determine, via the stimulation programmer circuit, a first stimulation current that results in a first metric value satisfying a clinical effect condition, the first metric value associated with a corresponding electrode current fractionalization; and generating a stimulation configuration for tissue stimulation via the stimulation programmer circuit, the stimulation configuration including the first stimulation current and the current fractionalization corresponding to the first metric value.

In Example 17, the subject matter of Example 16 optionally includes receiving a 3D triangulated surface representation of the tissue, and transforming the received 3D triangulated surface representation into the 3D voxelized model.

In Example 18, the subject matter of Example 16 optionally includes searching for a desired stimulation location with respect to positions of the plurality of electrodes. The desired stimulation location may be represented by at least a longitudinal coordinate and an angular coordinate in a coordinate space, and corresponding to the first metric value and its associated stimulation current.

In Example 19, the subject matter of Example 16 optionally includes the 3D voxelized model including 3D voxels each having a voxel volume. The determination of the first metric value for a stimulation location includes using a combination of the voxel volumes of the 3D voxels each weighted by a weight factor. The weight factor may be a positive scalar if the 3D voxel is situated in a target region, or a negative scalar if the voxel is situated in an avoidance region.

In Example 20, the subject matter of Example 19 optionally includes steps of sorting the 3D voxels in an ascending order of voxel current thresholds associated with the 3D voxels, the voxel current thresholds each determined according to the specified current fractionalization; computing adaptively the metric value by accumulating, from a beginning of the sorted 3D voxels, voxel metric effects representing volumes of the sorted 3D voxels each weighted by the weight factor of their respective regions, where the respective weight factors are signed scalars; identifying, from the sorted 3D voxels, a terminal voxel having a corresponding current threshold, the inclusion of the weighted volume of the terminal voxel resulting in a decrease of the adaptively generated metric value exceeding a specified tolerance; and determining, for the stimulation location, the first metric value to be the adaptively generated metric value, and the first stimulation current based on the terminal current threshold.

In Example 21, the subject matter of Example 19 optionally includes steps of generating amplitude bins of non-overlapping amplitude ranges sorted in an ascending order; categorizing each of the 3D voxels into one of the amplitude bins based on voxel current thresholds associated with the 3D voxels; computing, for each of the amplitude bins that includes a set of the categorized 3D voxels, a respective amplitude effect using a sum of voxel metric effect of the set of the categorized 3D voxels, the voxel metric effect representing a volume of a categorized 3D voxel weighted by a corresponding weight factor; computing adaptively a metric value by accumulating, from a beginning of the ordered amplitude bins, the amplitude effects of the ordered amplitude bins; and identifying, from the ordered amplitude bins, a terminal amplitude bin associated with a terminal amplitude range, the inclusion of an amplitude effect of the terminal amplitude bin resulting in a decrease of the adaptively generated metric value exceeding a specified tolerance; and determining, for the given stimulation location, the first metric value to be the generated metric value, and the first stimulation current based on the terminal amplitude range.

In Example 22, the subject matter of Example 16 optionally includes steps of generating one or more virtual electrode steering parameters for steering a virtual electrode on a graphical user interface; constructing a virtual electrode field model comprising a plurality of electrode primitives each having respective primitive voltage fields; constructing a voltage field of the virtual electrode using superposition of the primitive voltage fields of the plurality of electrode primitives each scaled by respective weight factors; and converting the voltage field of the virtual electrode to a voltage field of the plurality of electrodes using regression fitting.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
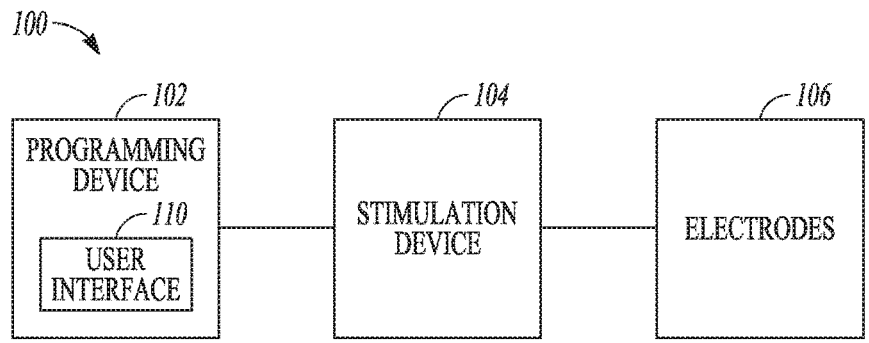
FIG. 1 illustrates an example of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a neurostimulation system configured to generate a stimulation configuration based on a model-based metric value indicative of clinical effect of electrostimulation on a target neural tissue, and to deliver therapeutic stimulation according to the stimulation configuration. The clinical effect may include information of therapeutic benefits and side effects associated with electrostimulation of the target neural tissue. In various examples, the neuromodulation system may include an implantable device configured to deliver neurostimulation (also referred to as neuromodulation) therapies, such as deep brain stimulation (DBS), spinal cord stimulation (SCS), peripheral nerve stimulation (PNS), and vagus nerve stimulation (VNS), and one or more external devices configured to program the implantable device for its operations and monitor the performance of the implantable device. While DBS is discussed as a specific example, the present subject matter may also be applied to program stimulation devices for delivering various types of neuromodulation therapies.

In various examples, the neurostimulation system may use a computer-generated three-dimensional (3D) voxelized model to determine a first metric value over a plurality of physiologic structures, analytically derived or user selected regions (e.g., of the brain or other areas), or combinations thereof. The neurostimulation system may determine one or more stimulation parameters that correspond to the first metric value, such as a stimulation current and an electrical current fractionalization across a plurality of electrodes. The first metric value may be referred to as a best metric value that exceeds a threshold metric value, or the largest metric value under a specific electrical current fractionalization. The current fractionalization refers to current distribution among electrodes, and may be represented by percentage cathodic current, percentage anodic current, or off (no current allocation). Although current fractionalization is discussed in this document, it is to be understood that voltage or electrical energy may similarly be fractionalized among the electrodes, which may result in a particular spatial distribution of the stimulation field.

In various examples, the neurostimulation system may determine a stimulation configuration including a stimulation location. The stimulation location may be represented by coordinates in a coordinate space, and corresponds to the best metric value. In various examples, the neurostimulation system may determine a virtual electrode state including one or more steering parameters. Through a user interface, a user may steer the virtual electrode according to the one or more virtual electrode steering parameters. The system may determine electrical current fractionalization across a plurality of electrodes based on the voltage field of the virtual electrode.

FIG. 1 illustrates, by way of example and not limitation, an embodiment of a neurostimulation system 100. In an example, the system 100 may be configured for DBS applications. Such DBS configuration includes various features that may simplify the task of the user in programming the stimulation device 104 for delivering DBS to the patient, such as the features discussed in this document.

The system 100 includes a programming device 102, a stimulation device 104, and electrodes 106. The electrodes 106 may be configured for placement on or near one or more neural targets in a patient. The stimulation device 104 may be configured to be electrically connected to the electrodes 106 and deliver neurostimulation energy, such as in the form of electrical pulses, to the one or more neural targets though the electrodes 106. In an example, the stimulation device 104 controls the delivery of neurostimulation energy according to a plurality of stimulation parameters, such as a selection of active electrodes for passing electrostimulation energy to the tissue, or stimulation pattern of the electrical pulses, among others. In various examples, at least some of the stimulation parameters are programmable by a user, such as a clinician.

The programming device 102 may be configured to be in communication with the stimulation device 104 via a wired or wireless link. The programming device 102 may provide the user with accessibility to user-programmable parameters. In the illustrated example, the programming device 102 may include a user interface 110 that allows a user to control the operation of the system 100 and monitor the performance of the system 100 as well as conditions of the patient including responses to the delivery of the neurostimulation. The user may control the operation of the system 100 by setting and/or adjusting values of the user-programmable parameters. In various examples, the user interface 110 may include a graphical user interface (GUI) that allows the user to create and/or edit graphical representations of various stimulation waveforms. The GUI may also allow the user to set and/or adjust stimulation fields each defined by a set of electrodes through which one or more neurostimulation pulses represented by a waveform are delivered to the patient. The stimulation fields may each be further defined by the current fractionalization across the set of electrodes. In various examples, neurostimulation pulses for a stimulation period (such as the duration of a therapy session) may be delivered to multiple stimulation fields.

In this document, a "user" includes a physician or other clinician or caregiver who treats the patient using the system 100; a "patient" includes a person who receives, or is intended to receive, neurostimulation via the system 100. In various examples, the patient may be allowed to adjust his or her treatment using system 100 to certain extent, such as by adjusting certain therapy parameters and entering feedback and clinical effect information.

Figure 2:
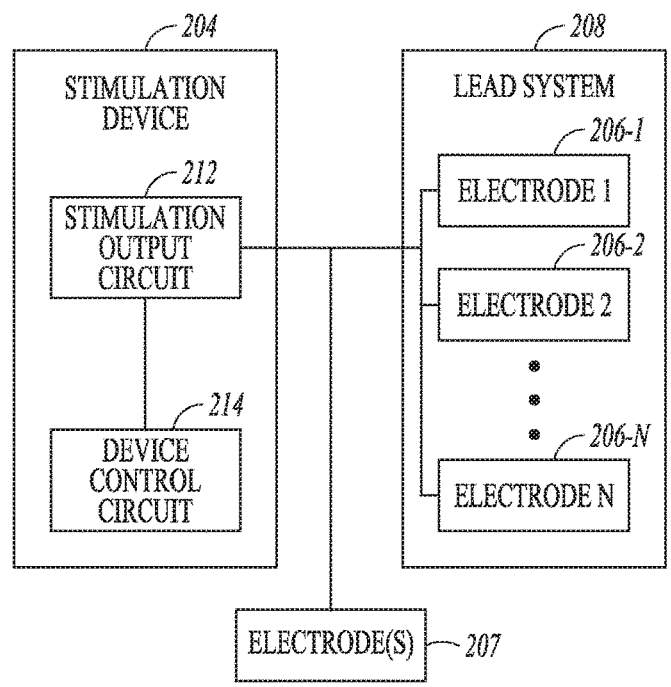
FIG. 2 illustrates an example of a stimulation device and a lead system that may be implemented in the neurostimulation system of FIG. 1.

FIG. 2 illustrates, by way of example and not limitation, an embodiment of a stimulation device 204 and a lead system 208, such as may be implemented in the neurostimulation system 100. The stimulation device 204 represents an embodiment of stimulation device 104, and includes a stimulation output circuit 212 and a device control circuit 214. The stimulation output circuit 212 may produce and deliver neurostimulation pulses. The device control circuit 214 may control the delivery of the neurostimulation pulses from stimulation output circuit 212 according to a plurality of stimulation parameters. The lead system 208 includes one or more leads each configured to be electrically connected to stimulation device 204 and a plurality of electrodes 206 (including electrode 206-1, 206-2, ..., 206-N) distributed in the one or more leads. Each of the electrodes 206 has an electrically conductive contact providing for an electrical interface between the stimulation output circuit 212 and patient tissue. In an example, the lead system 208 may include two leads each having eight electrodes.

The neurostimulation pulses are each delivered from stimulation output circuit 212 through a set of electrodes selected from electrodes 206. In various examples, the neurostimulation pulses may include one or more individually defined pulses, and the set of electrodes may be individually definable by the user for each of the individually defined pulses or each of collections of pulse intended to be delivered using the same combination of electrodes. In various examples, one or more additional electrodes 207 (referred to as reference electrodes) may be electrically connected to stimulation device 204, such as one or more electrodes each being a portion of or otherwise incorporated onto a housing of stimulation device 204. The neurostimulation may be delivered as a unipolar, bipolar, or multipolar stimulation. Monopolar stimulation uses a monopolar electrode configuration with one or more electrodes selected from the electrodes 206 and at least one electrode from electrode(s) 207. Bipolar stimulation uses a bipolar electrode configuration with two electrodes selected from the electrodes 206 and none of the electrode(s) 207. The bipolar stimulation may include balanced or unbalanced bipolar mode using a pair of electrodes on a lead, with the balancing current being applied to a reference electrode. Multipolar stimulation uses a multipolar electrode configuration with multiple (two or more) electrodes selected from electrodes 206 and none of the electrode(s) 207. In various examples, the number of leads and the number of electrodes on each lead depend on, for example, the distribution of target(s) of the neurostimulation and the need for controlling the distribution of electric field at each target.

Figure 3:
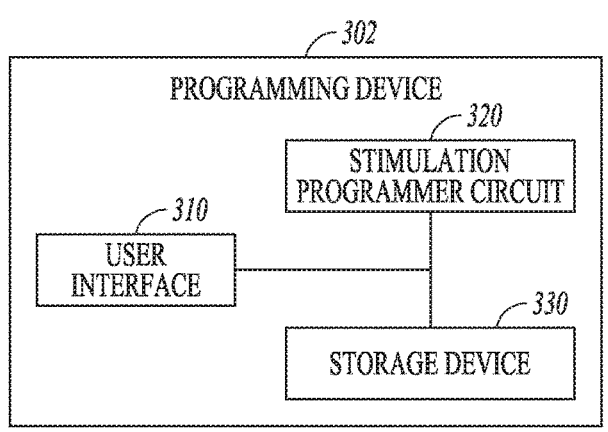
FIG. 3 illustrates an example of a programming device that may be implemented in the neurostimulation system of FIG. 1.

FIG. 3 illustrates, by way of example and not limitation, a programming device 302, which may be an embodiment of the programming device 102 and implemented in neurostimulation system 100. The programming device 302 may include a storage device 330, a stimulation programmer circuit 320, and a user interface 310. The stimulation programmer circuit 320 may be a part of control circuitry of the programming device 302, and is configured to support one or more functions allowing for programming of stimulation devices, such as stimulation device 104 including its various embodiments as discussed in this document. In various examples, the stimulation programmer circuit 320 may generate a plurality of stimulation parameters, collectively referred to as a stimulation configuration, that control the delivery of the neurostimulation pulses. In this document, a "stimulation configuration" may include the pattern of neurostimulation pulses including one or more stimulation fields, or at least various aspects or parameters of the pattern of neurostimulation pulses. In various examples, the stimulation configuration may specify a stimulation current (e.g., amplitude or energy of the stimulation) and an electrical current fractionalization across the plurality of electrodes. In some examples, the stimulation configuration may include a stimulation location and a stimulation current that corresponds to a best metric value. In various examples, the stimulation configuration may include a virtual electrode state that specifies a virtual electrode type, location of the virtual electrode in a coordinate space, and stimulation current associated with virtual electrode voltage field and virtual electrode location. Electrical current fractionalization across a plurality of electrodes may be determined based on the voltage field of the virtual electrode.

The storage device 330 may store information used by the stimulation programmer circuit 320, including the stimulation configuration, and information about a virtual electrode and steering of the virtual electrode on a graphical user interface. The user interface 310 represents an embodiment of user interface 110, and may be coupled to the stimulation programmer circuit 320. In various examples, the user interface 310 may allow for definition of a pattern of neurostimulation pulses for delivery during a neurostimulation therapy session by creating and/or adjusting one or more stimulation waveforms using a graphical method. The definition may also include definition of one or more stimulation fields each associated with one or more pulses in the pattern of neurostimulation pulses. In various examples, the user interface 310 may include a GUI that allows the user to define the pattern of neurostimulation pulses and perform other functions using graphical methods.

The circuits or subcircuits included in the neurostimulation system or devices, and their variations discussed in this document, may be implemented using a combination of hardware and software. For example, the circuit of user interface 110, device control circuit 214, stimulation programmer circuit 320, and stimulation programmer circuit 320, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4A:
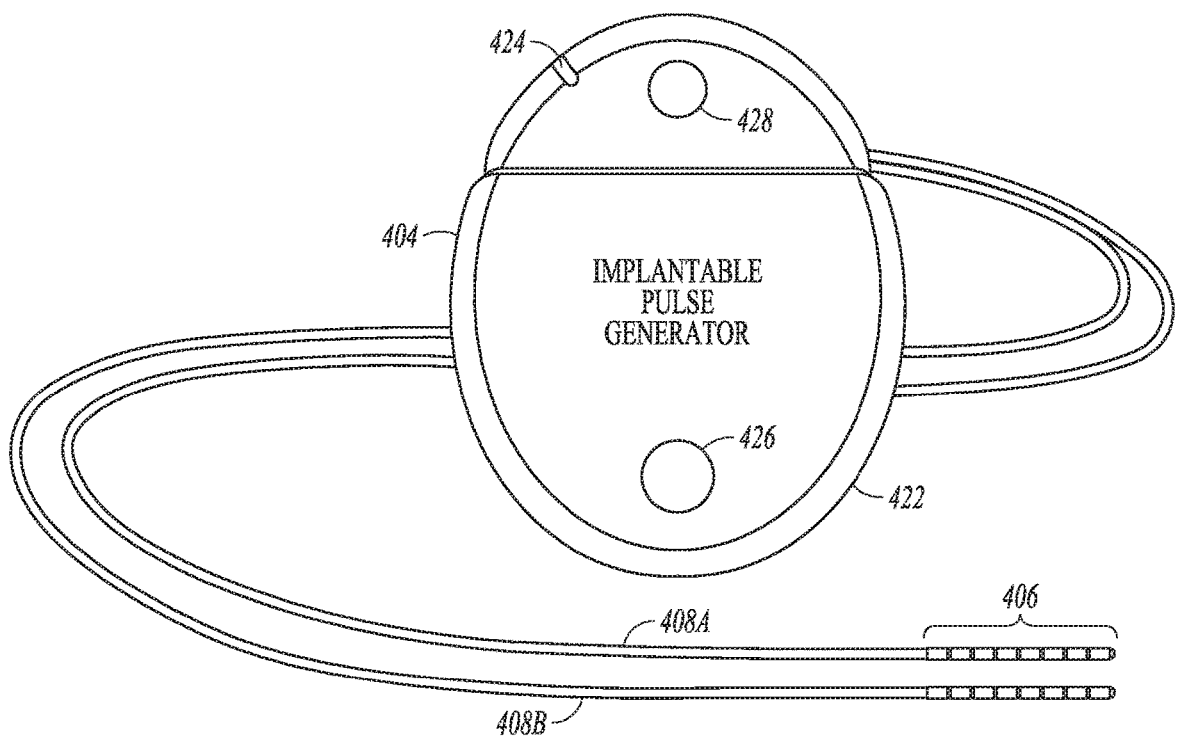
FIGS. 4A-4B illustrate examples of an implantable pulse generator (IPG) and an implantable lead system.
Figure 4B:
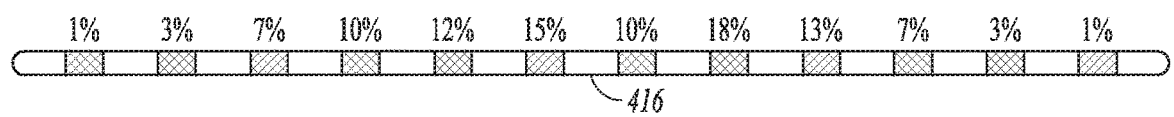

FIGS. 4A-4B illustrate, by way of example and not limitation, embodiments of an implantable pulse generator (IPG) 404 and an implantable lead system 408. The IPG 404 represents an example implementation of stimulation device 204, and may include a hermetically-sealed IPG case 422 to house the electronic circuitry of IPG 404. The IPG 404 may include an electrode 426 formed on the IPG case 433. The IPG 404 may include an IPG header 424 for coupling the proximal ends of leads 408A and 408B. The IPG header 424 may optionally include an electrode 428. Electrodes 426 and/or 428 represent embodiments of electrode(s) 207 and may each be referred to as a reference electrode. The IPG 404 may be communicatively coupled to a programming device, such as the programmer device 102 or the programming device 302, and configured to generate and deliver neurostimulation energy according to the stimulation configuration generated by the programming device 102 or 302.

The lead system 408 represents an example implementation of lead system 208, and includes, by way of example and not limitation, implantable leads 408A and 408B. As illustrated in FIG. 4A, the IPG 404 may be coupled to the implantable leads 408A-B at a proximal end of each lead. The distal end of each lead includes electrical contacts or electrodes 406 for contacting a tissue site targeted for electrical neurostimulation. By way of example and not limitation, the leads 408A-B each include eight electrodes 406 at the distal end. Other numbers and arrangements of leads 408A-B and electrodes 406 may also be used. In various examples, one or more of the electrodes 406 may be column electrodes (also known as ring electrodes), or segmented electrodes circumferentially disposed on a directional lead such as 408A or 408B.

The implantable leads and electrodes may be shaped and sized to provide electrical neurostimulation energy to a neural target, such as a brain, a nerve target of a spinal cord, or a peripheral nerve target. Neurostimulation energy may be delivered in a unipolar mode between an electrode selected from electrodes 406 and another electrode selected from electrodes 426 and 428, or in a balanced or unbalanced bipolar mode using a pair, or more, of electrodes on the same lead (e.g., lead 408A or lead 408B), with the balancing current being applied to reference electrodes 426 or 428. Neurostimulation energy may be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 may include a control circuit that controls delivery of the neurostimulation energy. The control circuit may include a microprocessor, a digital signal processor, application specific integrated circuit (ASIC), or other type of processor, interpreting or executing instructions included in software or firmware. The neurostimulation energy may be delivered according to specified (e.g., programmed) modulation parameters. Examples of setting modulation parameters may include, among other things, selecting the electrodes or electrode combinations used in the stimulation, configuring an electrode or electrodes as the anode or the cathode for the stimulation, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

The modulation parameters may additionally include fractionalization across electrodes. The fractionalization specifies distribution (e.g., the percentage) of the stimulation current, voltage, or electrical energy provided by an electrode or electrode combination, which affect the spatial distribution of the resultant stimulation field. In an example, current fractionalization specifies percentage cathodic current, percentage anodic current, or off (no current allocation). FIG. 4B illustrates a segment of an electrical neuromodulation lead that includes multiple electrodes 416, which may be an embodiment of the electrodes 406 of the lead 408A or 408B. Current is fractionalized across the active electrodes, and the electrodes 416 each may receive a respective current percentage. In the monopolar case, the fractionalized currents across the active electrodes add up to 100%. In the bipolar or multipolar cases, the fractionalized currents for at least one polarity add up to 100%, with any remaining percentage being allocated to the reference electrodes. Control of the current in terms of percentage allows precise and consistent distribution of the current among the electrodes even as the current amplitude is adjusted. It is suited for thinking about the problem as steering a stimulation locus, and stimulation changes on multiple contacts simultaneously to move the locus while holding the stimulation amount constant. In some examples, the current fractionalization may be defined by assigning an absolute current value (e.g., in milliampere, or mA) rather than a percentage to each electrode. Control of the current in terms of absolute values allows precise dosing of current through each specific electrode. It is suited for changing the current one contact at a time (and allows the user to do so) to shape the stimulation like a piece of clay (pushing/pulling one spot at a time).

The current fractionalization takes into account electrode/tissue coupling differences, which are the differences in how the tissue underlying each electrode reacts to electrical neuromodulation. In addition, electrodes on the distal portion of the lead may have lower gradient in the longitudinal direction, as electrical field strength may taper down at the ends of the lead. Current fractionalization may accommodate variation in the tissue underlying those electrodes. Various embodiments described herein implement a programmed algorithm to determine the appropriate fractionalization to achieve a desired neuromodulation field property.

Figure 5:
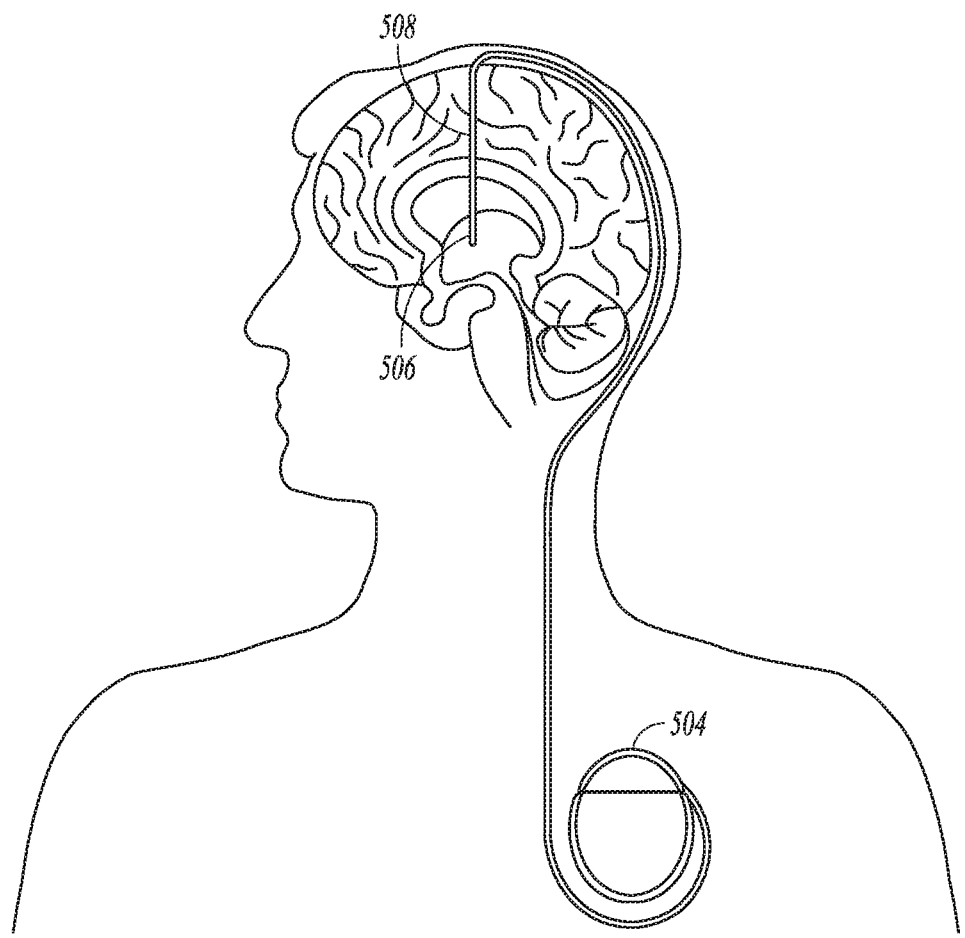
FIG. 5 illustrates an example of an IPG and an implantable lead system arranged to provide brain stimulation to a patient.

FIG. 5 illustrates, by way of example and not limitation, an embodiment of an IPG 504 and an implantable lead system 508 arranged to provide brain stimulation to a patient. An example of IPG 504 includes the IPU 404. The lead system 508 may include electrodes 506. An example of lead system 508 includes one or more of the leads 408A-B. An example of the electrodes 506 includes at least a portion of the electrodes 406. In the illustrated example, the IPG 504 and the implantable lead system 508 may provide Deep Brain Stimulation (DBS) to a patient, with the stimulation target being neuronal tissue in a subdivision of the thalamus of the patient's brain. Other examples of DBS targets include neuronal tissue of the globus pallidus (GPi), the subthalamic nucleus (STN), the pedunculopontine nucleus (PPN), substantia nigra pars reticulate (SNr), cortex, globus pallidus externus (GPe), medial forebrain bundle (MFB), periaquaductal gray (PAG), periventricular gray (PVG), habenula, subgenual cingulate, ventral intermediate nucleus (VIM), anterior nucleus (AN), other nuclei of the thalamus, zona incerta, ventral capsule, ventral striatum, nucleus accumbens, white matter tracts connecting these and other structures. The DBS targets may also include regions determined analytically based on side effects or benefits observed in one or more patients, as well as regions specified by the user.

Figure 6:
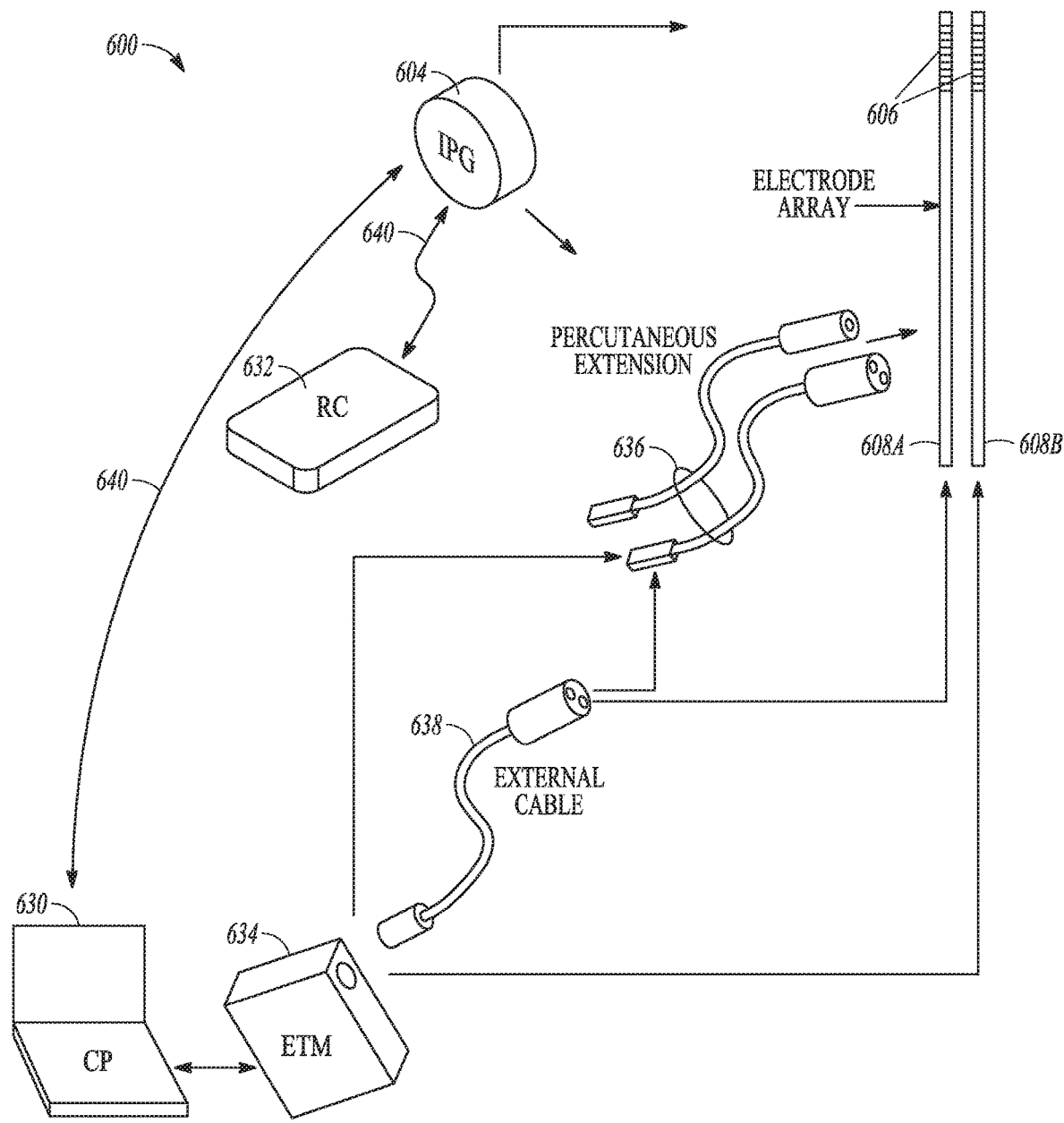
FIG. 6 illustrates an example of portions of a neurostimulation system.

FIG. 6 illustrates, by way of example and not limitation, an embodiment of portions of a neurostimulation system 600. The system 600 includes an IPG 604, implantable neurostimulation leads 608A and 608B, an external remote controller (RC) 632, a clinician's programmer (CP) 630, and an external trial modulator (ETM) 634. The system 600 may additionally include external sensors configured to sense one or more physiological parameters, such as a heart rate sensor, a pulse oximeter, an electrocardiogram sensor, an inertial sensor, or an electroencephalogram sensor, among others. The IPG 604 may be electrically coupled to the leads 608A and 608B directly or through percutaneous extension leads 636. The ETM 634 may be electrically connectable to the leads 608A and 608B via one or both of the percutaneous extension leads 636 and/or the external cable 638. The system 600 represents an embodiment of system 100, with IPG 604 representing an embodiment of the stimulation device 104, electrodes 606 of leads 608A and 608B representing the electrodes 106, and CP 630, RC 632, and the ETM 634 collectively representing the programming device 102.

The ETM 634 may be standalone or incorporated into the CP 630. The ETM 634 may have similar pulse generation circuitry as IPG 604 to deliver neurostimulation energy according to specified modulation parameters as discussed above. In an example, the ETM 634 is an external device and may be used as a preliminary stimulator after leads 408A and 408B have been implanted and used prior to stimulation with IPG 604 to test the patient's responsiveness to the stimulation that is to be provided by IPG 604. An external ETM 634 may be more easily configurable than the IPG 604.

The CP 630 may configure the neurostimulation provided by the ETM 634. If the ETM 634 is not integrated into the CP 630, then the CP 630 may communicate with ETM 634 using a wired connection (e.g., over a USB link) or by wireless telemetry such as using a wireless communications link. The CP 630 may also communicate with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. The IPG 604 may include the first coil and a communication circuit. The CP 630 may include or otherwise electrically connected to the second coil such as in the form of a wand that may be place near the IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one example, a communication range of an RF telemetry link is at least six feet but may be as long as allowed by the particular communication technology. RF antennas may be included, for example, in the header of the IPG 604 and in the housing of the CP 630, eliminating the need for a wand or other means of inductive coupling. An example is such an RF telemetry link is a Bluetooth® wireless link.

The CP 630 may be used to set modulation parameters for the neurostimulation after the IPG 604 has been implanted. This allows the neurostimulation to be tuned if the requirements for the neurostimulation change after implantation. The CP 630 may also upload information from or download information to the IPG 604.

The RC 632 also communicates with the IPG 604 using a wireless link 340. The RC 632 may be a communication device used by the user or given to the patient. The RC 632 may have reduced programming capability compared to the CP 630. This allows the user or patient to alter the neurostimulation therapy but does not allow the patient full control over the therapy. For example, the patient may be able to increase the amplitude of neurostimulation pulses or change the time that a preprogrammed stimulation pulse train is applied. The RC 632 may be programmed by the CP 630. The CP 630 may communicate with the RC 632 using a wired or wireless communications link. In some embodiments, the CP 630 is able to program the RC 632 when remotely located from the RC 632. In some examples, the RC 632 may download data to and upload data from the IPG 604.

Figure 7:
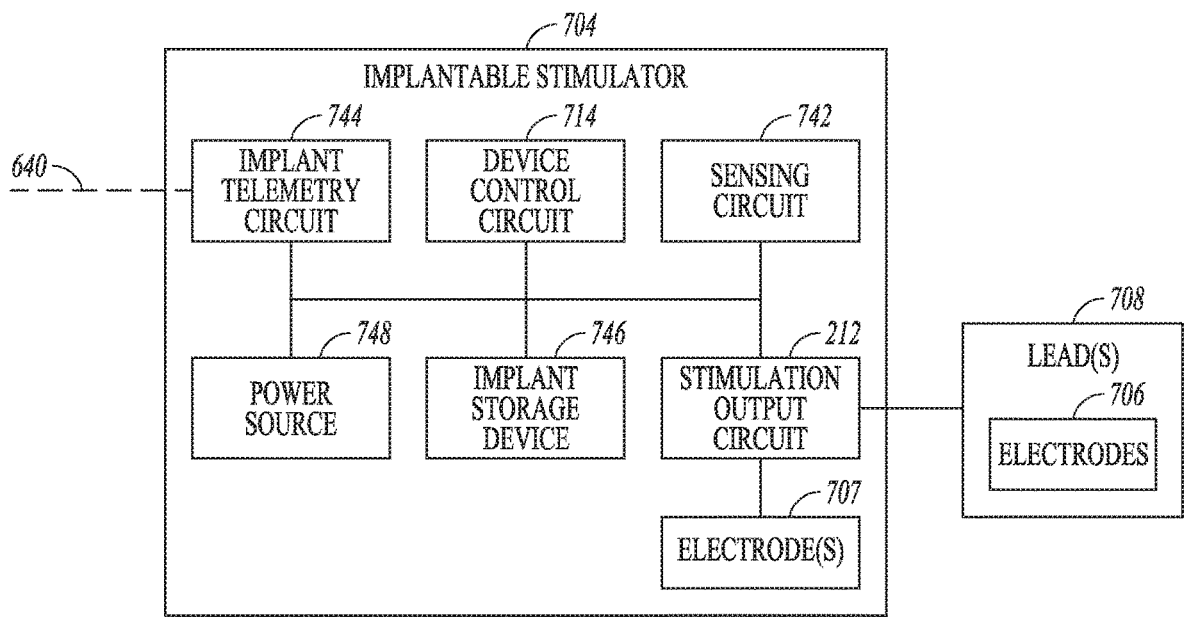
FIG. 7 illustrates an example of an implantable stimulator and one or more leads of an implantable neurostimulation system, such as the implantable neurostimulation system of FIG. 6.

FIG. 7 illustrates, by way of example and not limitation, an embodiment of implantable stimulator 704 and one or more leads 708 of an implantable neurostimulation system, such as the implantable system 600. The implantable stimulator 704 represents an embodiment of stimulation device 104 or 204 and may be implemented, for example, as the IPG 604. Lead(s) 708 represents an embodiment of lead system 208 and may be implemented, for example, as implantable leads 608A-B. The lead(s) 708 includes electrodes 706, which represents an embodiment of electrodes 106 or 206 and may be implemented as electrodes 606. In some examples, the implantable stimulator 704 may additionally be communicatively coupled to one or more external sensors configured to sense one or more physiological parameters, such as a heart rate sensor, a pulse oximeter, an electrocardiogram sensor, an inertial sensor, or an electroencephalogram sensor, among others.

The implantable stimulator 704 may include a sensing circuit 742 that is optional and required only when the stimulator needs a sensing capability, stimulation output circuit 212, a device control circuit 714, an implant storage device 746, an implant telemetry circuit 744, a power source 748, and one or more electrodes 707. The sensing circuit 742, when included and needed, senses one or more physiologic signals for purposes of patient monitoring and/or feedback control of the neurostimulation. Examples of the physiologic signals include neural and other signals each indicative of a condition of the patient that is treated by the neurostimulation and/or a response of the patient to the delivery of the neurostimulation. The stimulation output circuit 212 is electrically connected to electrodes 706 through one or more leads 708 as well as electrodes 707, and delivers each of the neurostimulation pulses through a set of electrodes selected from electrodes 706 and electrode(s) 707. The device control circuit 714 represents an embodiment of device control circuit 214, and controls the delivery of the neurostimulation pulses according to the stimulation configuration (including stimulation parameters) received from the programming device 102 or 302. In one embodiment, the device control circuit 714 controls the delivery of the neurostimulation pulses using the one or more sensed physiologic signals. The implant telemetry circuit 744 provides the implantable stimulator 704 with wireless communication with another device, such as the CP 630 or the RC 632, including receiving values of the plurality of stimulation parameters from the other device. The implant storage device 746 stores the received stimulation configuration, including values of the plurality of stimulation parameters. The power source 748 provides the implantable stimulator 704 with energy for its operation. The power source 748 may include a battery. In one embodiment, the power source 748 includes a rechargeable battery and a battery charging circuit for charging the rechargeable battery. The implant telemetry circuit 744 may also function as a power receiver that receives power transmitted from an external device through an inductive couple. The electrode(s) 707 allow for delivery of the neurostimulation pulses in the monopolar mode or unbalanced bipolar mode. Examples of the electrode(s) 707 include electrode 426 and electrode 418 in IPG 404 as illustrated in FIG. 4A.

In an example, the implantable stimulator 704 may be used as a master database. A patient implanted with implantable stimulator 704 (such as may be implemented as IPG 604) may therefore carry patient information needed for his or her medical care when such information is otherwise unavailable. The implant storage device 746 may be configured to store such patient information. For example, the patient may be given a new RC 632 and/or travel to a new clinic where a new CP 630 is used to communicate with the device implanted in him or her. The new RC 632 and/or CP 630 may communicate with the implantable stimulator 704 to retrieve the patient information stored in implant storage device 746 through the implant telemetry circuit 744 and the wireless communication link 640, and allow for any necessary adjustment of the operation of the implantable stimulator 704 based on the retrieved patient information.

In various examples, the patient information to be stored in the implant storage device 746 may include, for example, positions of lead(s) 708 and electrodes 706 relative to the patient's anatomy (transformation for fusing computerized tomogram (CT) of post-operative lead placement to magnetic resonance imaging (MRI) of the brain), clinical effect data, objective measurements using quantitative assessments of symptoms (e.g., using micro-electrode recording, accelerometers, and/or other sensors), and/or other information considered important or useful for providing adequate care for the patient. In various examples, the patient information to be stored in implant storage device 746 may include data transmitted to implantable stimulator 704 for storage as part of the patient information and data acquired by implantable stimulator 704, such as by using sensing circuit 742.

In various examples, the sensing circuit 742 (if included), stimulation output circuit 212, device control circuit 714, implant telemetry circuit 744, implant storage device 746, and power source 748 may be encapsulated in an implantable housing or case, such as the hermetically-sealed IPG case 422. The electrode(s) 707 may be formed or otherwise incorporated onto implantable housing or case. In numerous examples, the lead(s) 708 are implanted such that the electrodes 706 are placed on and/or around one or more targets to which the neurostimulation pulses are to be delivered, while the implantable stimulator 704 is subcutaneously implanted and connected to the lead(s) 708 at the time of implantation.

Figure 8:
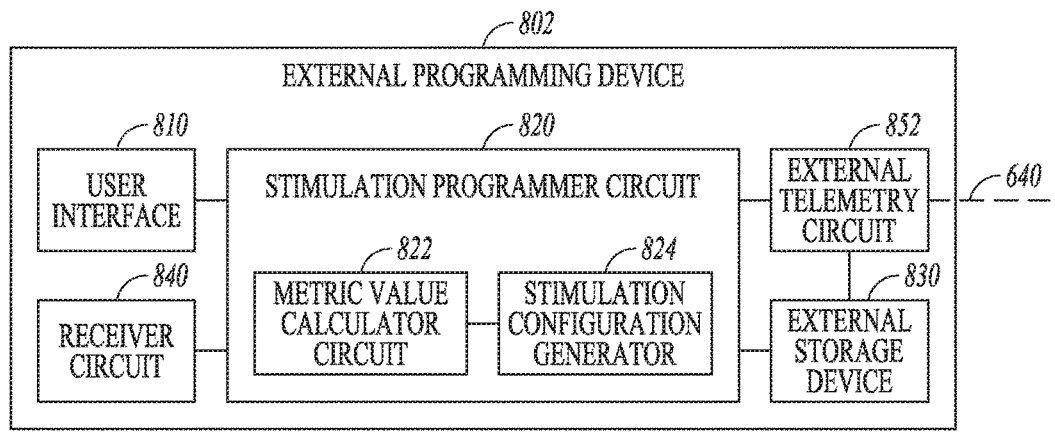
FIG. 8 illustrates an example of an external programming device of an implantable neurostimulation system.

FIG. 8 illustrates, by way of example and not limitation, an embodiment of an external programming device 802 of an implantable neurostimulation system, such as the system 600. The external programming device 802 represents an embodiment of programming device 102 or 302, and may be implemented, for example, as the CP 630 and/or the RC 632. In the illustrated example, the external programming device 802 includes a user interface 810, a receiver circuit 840, a stimulation programmer circuit 820, an external storage device 830, and an external telemetry circuit 852.

The user interface 810, which is an embodiment of user interface 310, allows a user to perform various patient monitoring and electrostimulation programming tasks. An example of the user interface 810 includes a graphical user interface. The user interface 810 may include a display screen and a user input device. The display screen is configured to display one or more of the computer-generated 3D voxelized tissue model, stimulation configuration including various stimulation parameters, or virtual electrodes, among other control parameters. In an example, clinical effect information associated with stimulation of a particular tissue site may be displayed on the displayed screen, including information about therapeutic benefits and side effects produced by the stimulation. The benefits or side effects may take a form of a score or a graphical representation. The user input device may include one or more of a touchscreen, a keyboard, a keypad, a touchpad, a trackball, a joystick, or a mouse. The user input device allows a user to confirm, reject, or adjust the automatically generated stimulation configuration, as discussed in this document. In an example, a user may use the user input device to adjust one or more stimulation parameters, such as weight factors associated with various clinical effect-indicated physiologic structures or analytically determined structures used by the 3D voxelized tissue model. In another example, a user may use the user input device to adjust an automatically generated virtual electrode state, such as adjusting one or more steering parameters for steering a virtual electrode. In yet another example, a user may use the user input device to provide virtual electrode steering parameters, or modify a previously generated virtual electrode steering parameters (e.g., longitudinal coordinate and/or angular coordinate of the virtual electrode).

The receiver circuit 840 may receive a 3D voxelized model of a tissue as a target of electrostimulation, such as particular brain tissue as a target of deep brain stimulation (DBS). A voxel represents a volumetric element of a computerized physiologic structure or analytically determined structure, such as a computerized tissue representation, in a 3D space. A voxel may have specified size in each dimension, such as 0.5 mm or less. The 3D voxelized model may include a computer-generated graphic model representing volumetric tissue elements and their responses to the electrostimulation. In an example, the 3D voxelized model comprises an array of 3D voxels each specified as belonging to one of a plurality of physiologic structures, such as a target region or an avoidance region. A target region may refer to a physiologic structure, analytically derived or user selected regions (e.g., of the brain or other areas), or combinations thereof. The target region may be associated with known therapeutic benefits of the electrostimulation. An avoidance region may refer to a physiologic structure, analytically derived or user selected regions, or combinations thereof that are associated with a known side effect of the electrostimulation. Each target or avoidance region may be assigned a corresponding weight factor w correlated to a clinical outcome of electrostimulation delivered at respective physiologic structures, such as a therapeutic benefit or a side effect. For example, a target region ($S^+$) may be associated with a positive weight factor, and an avoidance region ($S^-$) may be associated with a negative weight factor. The absolute value of the weight factor signifies relative significance of the clinical outcome. In an example of DBS, an avoidance structure that produces a slight slur (a side effect of DBS) may be of less clinical significance or importance than an avoidance structure that causes seizure (another side effect of DBS). As such, a weight factor with a larger absolute value may be assigned to the seizure-causing structure. In various examples, a user may use the user input device of the user interface 810 to assign or adjust weight factors for various regions based on known clinical effects of the electrostimulation on the respective regions.

Each of the 3D voxels of the received 3D voxelized model has a voxel volume and a voxel value. The voxel volume represents a geometric size of the voxel. The voxel value may, among other possibilities, represent a likelihood that the corresponding voxel volume may contribute to the clinical outcome (therapeutic benefit or side effect). For example, a voxel value of 0.8 indicates that the voxel has 80% chance of having the benefit or side effect of the structure to which it is a part. In another example, multiple regions could be represented in the same structure of voxels, where the voxel values represent the relative weights of the various regions (e.g., the slur versus the seizure inducing regions). Each set of voxels may either belong to the target regions (with therapeutically beneficial effects) or avoidance regions (with side effects). In yet another example, all regions, including both the target and avoidance regions, may be represented in the same set of voxels, in which case all the voxels in the avoidance region are assigned negative voxel values, and all the voxels are assigned positive voxel values. In an example, a user may adjust one or more of the weight factors w associated with various target structures and avoidance structures, the voxel volumes, or the voxel values associated with the 3D voxels, such as via the user interface 810.

In an example, the receiver circuit 840 may receive a 3D triangulated surface representation of the tissue. The 3D triangulated surface representation may include a digitized image of contours of the regions (e.g., target structures and avoidance structures). An image processing circuit (not shown) coupled to the stimulation programmer circuit 820 may be configured to transform the 3D triangulated surface representation into a 3D voxelized model. In an example, the voxelization may involve linear or non-linear interpolation of the complex geometry of the 3D triangulated surface, produce a wire-mesh representation of the surface, and generate a set of 3D voxels. In some examples, the voxelized surface may further be smoothed such as by convolving with a smoothing kernel. The 3D voxelized model, along with the voxel volumes and the voxel values associated with the 3D voxels, may be provided to the stimulation programmer circuit 820 for determining a metric value.

The stimulation programmer circuit 820 represents an embodiment of stimulation programmer circuit 320, and may generate a stimulation configuration (e.g., a plurality of stimulation parameters) to be transmitted to the implantable stimulator 704. The stimulation programmer circuit 820 may be a part of external control circuitry in the external programming device 802, and implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The stimulation programmer circuit 820 may include circuit sets comprising one or more other circuits or sub-circuits, including a metric value calculator circuit 822 and a stimulation configuration generator circuit 824, as depicted in FIG. 8. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The metric value calculator circuit 822 may be configured to determine, for each of the regions, a respective metric value (MV) using the received 3D voxelized model. The MV represents a clinical effect of electrostimulation on the tissue according to a stimulation current and fractionalization of electrical current. In an example, the MV may be computed using a weighted combination of the volumes of the array of 3D voxels in the voxelized model. For example, for each 3D voxel i in a region j (either a target region or an avoidance region), a corresponding voxel effect (X(i, j)) representing voxel i's contribution to the MV for the region j, may be computed using the following equation:

$$X(i,j) = \text{vol}(j) * w(j) * \text{val}(i,j) \quad (1)$$

where vol(j) represents the voxel volume for voxel i, and w(j) represents the weight factor associated with the region to which the voxel i belongs (region j in this case), and val(i, j) represents the voxel value for voxel i. All the voxels in a particular region (e.g., region j) have the same voxel volume (vol(j)), and all the voxels in a particular region (e.g., region j) share the same weight (w(j)) of that region. The voxel-specific weight factor w(i, j) is a positive scalar if the 3D voxel i is situated in a target region, or a negative scale if the 3D voxel i is situated in an avoidance region. Therefore, the 3D voxels situated in a target region ($S^+$) have positive voxel effects X, and the 3D voxels situated in an avoidance region ($S^-$) have negative voxel effects X. The absolute value of the weight factor represents relative significance of the clinical outcome. In an example, the weight factor is a non-zero scalar between −1 and 1. The MV for the region j may be determined using a combination of voxel effects across all N voxels within the region j in the 3D voxelized model that have been stimulated, according to the following Equation:

$$MV = X(1,j) + X(2,j) + \ldots + X(N,j) \quad (2)$$

Associated with the MV is a stimulation current (Is) applied to the 3D voxels in the region. The MV may also be associated with electrical current fractionalization ($F_I$) across a plurality of electrodes that deliver stimulation energy to the region. The relationship among $I_S$, $F_I$, and the MV may be represented as: Is=f (MV, $F_I$), where f is a linear or nonlinear function. The MV represents a clinical outcome with tissue recruitment from a physiologic or analytically determined region. The tissue recruitment may be represented by the number of 3D voxels recruited and their respective voxel effect X(i, j).

The stimulation configuration generator circuit 824 may determine a stimulation configuration corresponding to a best metric value ($MV_{opt}$) that satisfies a specific optimization condition. In an example, $MV_{opt}$ may be identified as a metric value that exceeds a threshold metric value $MV_{TH}$. In another example, $MV_{opt}$ may be identified as the largest MV under a specific electrical current fractionalization According to the relationship Is=f (MV, $F_I$) as discussed above, associated with the $MV_{opt}$ (e.g., a maximum MV under the specific electrical current fractionalization $F_I$) is a corresponding Is. In an example, the stimulation configuration generator circuit 824 may determine a minimal stimulation current ($I_{min}$) that results in an $MV_{opt}$. The $MV_{opt}$ may be associated with a specific current fractionalization $F_I^*$. The relationship among $I_{min}$, $F_I^*$, and $MV_{opt}$ may be represented as: $I_{min}$=($MV_{opt}$, $F_I^*$). The minimal stimulation current $I_{min}$ and the current fractionalization $F_I^*$ that correspond the best metric value $MV_{opt}$ may be programmed into the implantable stimulator 704 to generate and deliver electrostimulation to the tissue. Examples of determining the $I_{min}$ that results in the best metric value $MV_{opt}$ under a specified electrical current fractionalization $F_I$ are discussed below, such as with reference to FIGS. 10A-10B.

The external telemetry circuit 852 provides the external programming device 802 with communication with another device, such as the implantable stimulator 704 via the wireless communication link 640. The communication between the external programming device 802 and the implantable stimulator 704 may include transmission of the stimulation configuration to the implantable stimulator 704, including the minimal stimulation current $I_{min}$ and the current fractionalization $F_I^*$ associated with the best metric value $MV_{opt}$, among other stimulation parameters, and receiving patient physiologic data and implantable device status data from the implantable stimulator 704. Data transmission between the external programming device 802 and the implantable stimulator 704 may be continuous, periodic at a specified period, or triggered by a user command or a specific event. In one embodiment, the external telemetry circuit 852 may also transmit power to the implantable stimulator 704 through a charging circuit such as an inductive couple.

In various examples, the wireless communication link 640 may include an inductive telemetry link (near-field telemetry link) and/or a far-field telemetry link (RF telemetry link). For example, because DBS is often indicated for movement disorders that are assessed through patient activities, gait, balance, etc., allowing patient mobility during programming and assessment is useful. Therefore, when the system 600 is intended for applications including DBS, the wireless communication link 640 may include at least a far-field telemetry link, either near field or far field, that allows for communications between the external programming device 802 and the implantable stimulator 704 over a relative long distance, such as up to about 20 meters. In various examples, the external telemetry circuit 852 and implant telemetry circuit 744 each may include an antenna and RE circuitry configured to support such wireless telemetry.

The external storage device 830 may store the stimulation configuration, including the minimal stimulation current $I_{min}$ and the current fractionalization $F_I^*$ associated with the best metric value $MV_{opt}$, among other stimulation parameters and building blocks for defining one or more stimulation waveforms. The one or more stimulation waveforms may each be associated with one or more stimulation fields and represent a pattern of neurostimulation pulses to be delivered to the one or more stimulation field during the neurostimulation therapy session. In various examples, each of the one or more stimulation waveforms may be selected for modification by the user and/or for use in programming a stimulation device such as the implantable stimulator 704 to deliver a therapy. In various examples, each waveform in the one or more stimulation waveforms is definable on a pulse-by-pulse basis, and the external storage device 830 may include a pulse library that stores one or more individually definable pulse waveforms each defining a pulse type of one or more pulse types. The external storage device 830 may also store one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various examples, each field of the one or more individually definable fields is defined by the set of electrodes through which the neurostimulation pulse is delivered and a current distribution of the neurostimulation pulse over the set of electrodes.

In various examples, the stimulation configuration, including the minimal stimulation current $I_{min}$ and the current fractionalization $F_I^*$ associated with the best metric value $MV_{opt}$, among other stimulation parameters, may be displayed on the display screen of the user interface 810. In an example, a user may adjust the stimulation configuration using a user input device through a GUI of the user interface 810. The adjusted stimulation configuration may be stored in the external storage device 830. In various examples, the stimulation programmer circuit 820 may check values of the plurality of stimulation parameters against safety rules to limit these values within constraints of the safety rules. In one embodiment, the safety rules are heuristic rules.

Figure 9:
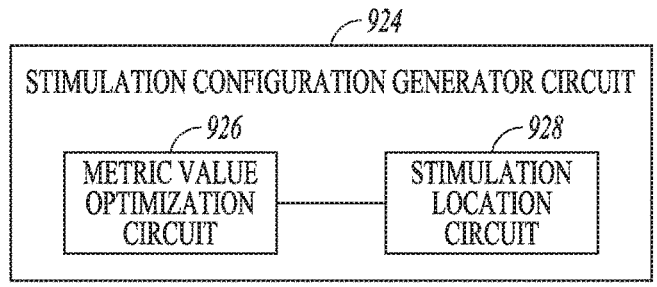
FIG. 9 illustrates an example of a stimulation configuration generator for generating a stimulation configuration including a stimulation location associated with a best metric value.

FIG. 9 illustrates, by way of example and not limitation, an embodiment of a stimulation configuration generator circuit 924, which is an embodiment of the stimulation configuration generator circuit 824. The stimulation configuration generator circuit 924 is configured to generate a stimulation configuration including a stimulation location associated with a first metric value, referred to as a best metric value ($MV_{opt}$), that exceeds a threshold $MV_{TH}$ or satisfies a specific optimization condition. The stimulation location may be represented by target coordinates of a virtual electrode in a coordinate space. In an example, the coordinate space may be spanned by at least a longitudinal coordinate and an angular coordinate, and the target coordinates may be represented by a longitudinal-angular coordinate pair.

In an example, the target coordinates may be measured with reference to positions of a reference electrode from a plurality of stimulation electrodes on a longitudinal lead, such as one of the leads 408A or 408B. In an example, the lead may include a directional lead with segmented electrodes distributed on a circumference of the directional lead. For such a directional lead, the reference electrode positions may be represented by a reference longitudinal position ($Z_0$) along the length of the lead and a reference angular position ($\theta_0$) around the circumference of the lead. The target coordinates may be represented by a Z-offset ($Z_d$) relative to the longitudinal position $Z_0$, and a rotation angle ($\theta_d$) relative to the angular position $\theta_0$. In an example, the reference longitudinal position $Z_0$ may be taken as a center of a most distal electrode on the lead, and the Z-offset $Z_d$ may be measured as a distance (e.g., in millimeters) along the lead away from $Z_0$. In an example, the reference angular position ($\theta_0$) may correspond to a reference plane through the center of a specified segmented electrode on a circumference of the directional lead and the longitudinal axis of the lead, and $\theta_d$ may be measured as an angle of rotation from the reference plane. In an example, multiple segmented electrodes on a directional lead may each be indexed (e.g., electrode 1, electrode 2, etc.). The electrode indexing may be tied to radio-opaque orientation marker at another point on the directional lead that would allow a clinician to determine the orientation of the lead. A user may specify, such as via the user interface 310, one of the multiple segmented electrodes as the electrode that defines the reference plane.

As illustrated in FIG. 9, the stimulation configuration generator circuit 924 includes a metric value optimization circuit 926 and a stimulation location circuit 928. The metric value optimization circuit 926 may determine a best metric value ($MV_{opt}$) using the calculated metric values provided by the metric value calculator circuit 822. The $MV_{opt}$ corresponds to the minimal stimulation current $I_{min}$ and an optimal longitudinal-angular coordinate pair ($Z_{opt}$, $\theta_{opt}$). As previously discussed with reference to FIG. 8, the best metric value $MV_{opt}$ is associated with the minimal stimulation current $I_{min}$ and a corresponding current fractionalization $F_I^*$. The optimal longitudinal-angular coordinate pair ($Z_{opt}$, $\theta_{opt}$) may be correlated to the specific current fractionalization $F_I^*$. The metric value optimization circuit 926 may vary the stimulation location ($Z_d$, $\theta_d$) in the coordinate space to search for the $MV_{opt}$. In an example, the metric value optimization circuit 926 may search a subspace of the coordinate space defined by $Z_d$ within a specified range (e.g., $Z_{d-min} \leq Z_d \leq Z_{d-max}$) and $\theta_d$ within a specified range (e.g. $0 \leq \theta_d < 360°$) for a coordinate pair that maximizes the metric value. One example of the search method is brute force search (also known as exhaustive search), which enumerates all candidate coordinates ($Z_d$, $\theta_d$) in a search space (such as a subspace defined as $Z_{d-min} \leq Z_d \leq Z_{d-max}$ and $0 \leq \theta_d < 360°$) and evaluates metric values at each of the enumerated candidate locations. In another example, the search for ($Z_{opt}$, $\theta_{opt}$) may be performed in a closed-loop fashion, such as using an iterative optimization method. Examples of the iterative optimization methods include gradient descent search, genetic algorithms, simulated annealing, random coordinate descent, particle swarm, fuzzy logic, among other machine-learning search algorithms.

In an example, the stimulation configuration generator circuit 924 may search for the optimal location ($Z_{opt}$, $\theta_{opt}$) using gradient descent of metric value in the coordinate space. The gradient descent method involves an iterative update of the longitudinal-angular coordinate pair ($Z_d$, $\theta_d$) using a metric gradient vector. In an example, the metric value optimization circuit 926 may determine an initial best metric value $MV_{opt}(0)$ at initial coordinates ($Z_d(0)$, $\theta_d(0)$). From the $MV_{opt}(0)$, a minimal stimulation current $I_{min}(0)$ may be derived, such as based on voxel ranking or current amplitude ranking, as to be discussed later in this document with reference to FIGS. 10A-10B. A 3D triangulated surface may be constructed in the coordinate space using three points, denoted by (P1, P2, P3). The three points each have their respective metric value and coordinates. The metric value optimization circuit 926 may determine a metric gradient vector ($\nabla M_{P1P2P3}$) using the three points (P1, P2, P3). The metric gradient vector points to a direction of increase in the metric value. The metric value optimization circuit 926 may update the coordinate pair ($Z_d(0)$, $\theta_d(0)$) to a new coordinate pair ($Z_d(1)$, $\theta_d(1)$) using the metric gradient vector $\nabla M_{P1P2P3}$. A new best metric value $MV_{opt}(1)$ may be determined at the new coordinates ($Z_d(1)$, $\theta_d(1)$). From the $MV_{opt}(1)$, a minimal stimulation current $I_{min}(1)$ may be derived based on voxel ranking or current amplitude ranking, as to be discussed later in this document with reference to FIGS. 10A-10B. The metric value optimization circuit 926 may then determine a point (Q) along the direction of the determined metric gradient vector, and construct another 3D triangulated surface using the point Q and two points (Px, Py) selected from the three points (P1, P2, P3) that are closer to the point Q. A new 3D triangulated surface may be constructed using the three points (Px, Py, Q). The metric value optimization circuit 926 may then determine a new metric gradient vector ($VM_{PxPyQ}$) using the three points (Px, Py, Q).

The search process for the optimal coordinate pair may continue until a specified iteration exit criterion has been met. In an example, the search process may stop when a specified number of iterations of coordinate update has been reached. In another example, the search process may stop when the best metric value at the present iteration satisfies a specific convergence criterion, such as when the difference between the best metric values before and after the present iteration falls below a threshold δ: $|MV_{opt}(k)-MV_{opt}(k-1)|<\delta$. In yet another example, the search process may stop when the coordinate pair at the present iteration satisfies a specific convergence criterion, such as when the difference D (e.g., a distance in the coordinate space) between the coordinate pairs before and after the present iteration falls below a threshold φ: $D((Z_d(k), \theta_d(k)), (Z_d(k-1), \theta_d(k-1))) < \varphi$. Upon a satisfaction of the iteration exit criterion, the optimal metric value $MV_{opt}(n)$ at the last iteration (e.g., n-th iteration), which is associated with the coordinate pair $(Z_d(n), \theta_d(n))$, may be determined. A corresponding smallest stimulation current $I_{min}(n)$ may be derived from $MV_{opt}(n)$. In an example, the minimal stimulation current $I_{min}$ may be determined only after the iteration exit criterion is satisfied (i.e., at the last iteration of computing the $MV_{opt}(n)$). For each of the intermediate iterations prior to iteration exit criterion being satisfied (i.e., for all k<n), the metric value optimization circuit 926 may determine the best metric value at the intermediate iteration $MV_{opt}(k)$ and associated coordinates $(Z_d(k), \theta_d(k))$ without determining the minimal stimulation currents $I_{min}(k)$.

The stimulation location circuit 928 may determine the optimal longitudinal-angular coordinate pair $(Z_{opt}, \theta_{opt})$ that corresponds to the best metric value $MV_{opt}$ at a lowest stimulation current $I_{min}$. The optimal coordinate pair $(Z_{opt}, \theta_{opt})$ and the lowest stimulation current $I_{min}$ that produces the $MV_{opt}$ are collectively referred to as a "stimulation state." The stimulation location circuit 928 may provide the stimulation state to the implantable stimulator 704 via the external telemetry circuit 852 and the wireless communication link 640. The implantable stimulator 704 may generate and deliver electrostimulation according to the stimulation state. In an example, a user (e.g., a clinician) may manually adjust the stimulation state (e.g., the stimulation current) from an initial value (e.g., zero or another value lower than the programmed $I_{min}$), and gradually titrate the actual stimulation current to a level up to the programmed $I_{min}$. In another example, the stimulation state and $MV_{opt}$ may be stored in the external storage device 830. Additionally or alternatively, the stimulation state and $MV_{opt}$ may be displayed on a display screen of the user interface 810, where a user (e.g., a clinician) may accept, reject, or otherwise modify the stimulation state.

The simulation configuration generator circuit 924 and associated methods discussed herein may improve the efficiency and accuracy for searching for an optimal location $(Z_{opt}, \theta_{opt})$ corresponds to the best metric value $MV_{opt}$ at a lowest stimulation current $I_{min}$. Using the known clinical effects on various structures of the tissue in response to stimulation (e.g., as represented by weight factors assigned to each target or avoidance structure), the simulation configuration generator circuit 924 provides a better starting point for searching the treatment space (e.g., stimulation location). This may reduce the search time and simplify the optimization process, and allow the patient a higher quality of treatment with desirable clinical effect.

Figure 10A:
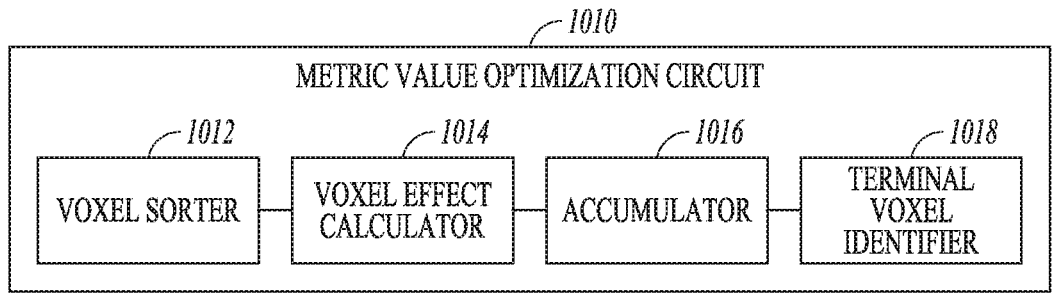
FIGS. 10A-10B illustrate examples of metric value optimization circuits for determining the lowest stimulation current that results in the best metric value for a particular electrode fractionalization.
Figure 10B:
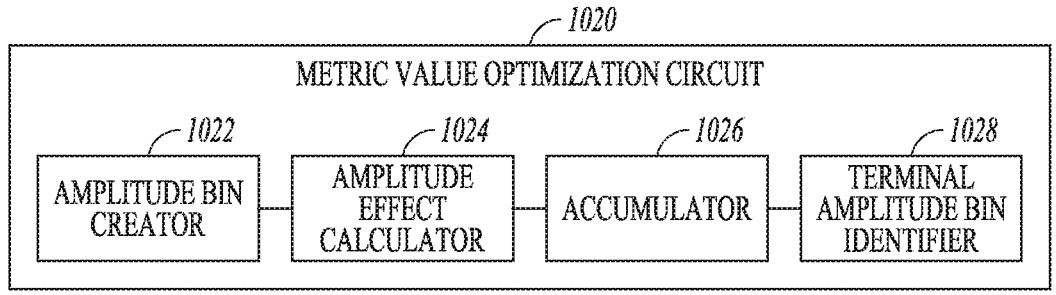

FIGS. 10A-10B illustrate, by way of example and not limitation, embodiments of metric value optimization circuits 1010 and 1020 each configured to determine the lowest stimulation current $I_{min}$ that results in the best metric value $MV_{opt}$ under a specified electrical current fractionalization or for a specified stimulation location. The best metric value $MV_{opt}$ is indicative of a specific clinical outcome, such as a desired balance between the therapeutic benefits and side effects. The metric value optimization circuits 1010 and 1020 are embodiments of the metric value optimization circuit 926.

The metric value optimization circuits 1010 as illustrated in FIG. 10A may include one or more of a voxel sorter 1012, a voxel effect calculator 1014, an accumulator 1016, and a terminal voxel identifier 1018. The voxel sorter 1012 may sort the 3D voxels of the 3D voxelized model of the tissue received from the receiver circuit 840. The 3D voxels each have their respective voxel current thresholds ($I_{th}$) representing minimum current required to activate the tissue voxel and produce a clinical effect for a specific current fractionalization. The $i_{th}$ may be provided by a system user such as via the receiver circuit 840, or generated by a threshold generator based on the specified current fractionalization. In an example, the threshold generator may be based on a deterministic equation such as one describing the current-distance relationship. In an example, the threshold generator may be based on a computational model of the current or energy required to produce a specified target effect. Registry data taken from a clinical database correlating patient-specific electrode placements and stimulation current with therapeutic benefits and side effects may be used to estimate the current threshold. In another example, the threshold generator may sample pre-generated tables for various steering coordinates. In yet another example, the threshold generator may use the fractionalization to determine a voltage field along a physiological target an axon) in a regular grid in Z-θ space through superposition. For each voltage field, the threshold generator may run a simulation of time variant response to the application of that voltage field using one or more pulse shapes to determine the $I_{th}$ value. In another example, the threshold generator may first determine the voltage field along each physiological target, then determine predictors for use in a machine learning engine to produce the $I_{th}$ value.

The voxel sorter 1012 may sort the 3D voxels in an ascending order of the $I_{th}$ associated with the 3D voxels. The voxel effect calculator 1014 may calculate, for each of the 3D voxels, a voxel metric effect using voxel volume and voxel value associated with each 3D voxel, as well as the weight factor associated with the structure or region to which the voxel belongs, such as according to Equation (1) as discussed above with reference to the metric value calculator circuit 822.

The accumulator 1016 may generate the metric value (MV) adaptively by accumulating the voxel metric effects starting from the beginning of the sorted 3D voxels associated with the lowest voxel current threshold $I_{th}$. For example, the accumulation at (i+1)-th iteration may include the voxel metric effect X(i+1) representing a contribution of the (i+1)-th voxel of the sorted 3D voxels. The accumulation may be mathematically represented by Equation (3) as follows:

$$MV(i+1)=MV(i)+X(i+1) \qquad (3)$$

Because the voxel metric effect is a signed number, the accumulated metric value after each iteration may be greater than, or less than the accumulated metric value before that iteration. The terminal voxel identifier 1018 may evaluate the accumulated MV at each iteration against a specific criterion, and to identify a terminal voxel corresponding to an accumulated MV satisfying the specific criterion. The terminal voxel corresponds to the first voxel processed that has produces the optimal MV. In an example, the terminal voxel may be identified when an inclusion of X(m) results in a decrease of the accumulated metric value exceeding a specified tolerance, that is, $MV(m)<MV(m-1)$ and $MV(m-1)-MV(m)>\delta$. The terminal voxel identifier 1018 may determine, for the specific stimulation location or current fractionalization, the best metric $MV_{opt}$ to be the adaptively generated metric value MV(m), and the lowest stimulation current $I_{min}$ to be the current threshold $I_{th}(m)$ associated with the identified terminal voxel. In some examples, the stimulation current may be selected from a set of candidate current amplitude steps. The lowest stimulation current $I_{min}$ may be determined as the smallest step that is greater than or equal to the current threshold $I_{th}(m)$ associated with the identified terminal voxel. For example, the candidate amplitude steps may include 200 steps from 0 to 20 mA in 0.1 mA steps (i.e., 0, 0.1, 0.2, . . . , 19.9, and 20 mA). If $I_{th}(m)$ is 0.75 mA, then the $I_{min}$ may be determined to be 0.8 mA as it is the lowest step greater than 0.75 mA. In some examples, the $I_{min}$ may be determined further using MV values associated with the candidate amplitude steps.

The metric value optimization circuits 1020 as illustrated in FIG. 10B comprises an amplitude bin creator 1022, an amplitude effect calculator 1024, an accumulator 1026, and a terminal amplitude identifier 1028. The amplitude bin creator 1022 may discretize a specified stimulation current range (e.g., 0-20.0 mA) into different amplitude bins each defined by respective amplitude ranges. The amplitude ranges of the amplitude bins may be non-overlapping to allow for more accurate MV for each amplitude bin. The amplitude bins may be arranged in an ascending order of the amplitude ranges. For example, stimulation current ranging from 0 to 20.0 mA may be discretized in 0.1 mA steps, resulting in 200 amplitude bins of stimulation current: [0, 0.1 mA), [0.1, 0.2 mA), [0.2, 0.3 mnA), . . . , [19.9, 20 mA]. The amplitude bin creator 1022 may assign each of the 3D voxels to one of the amplitude bins based on the voxel current threshold ($I_{th}$) associated with the 3D voxels under a specific current fractionalization. This is referred to as voxel categorization. For example, a 3D voxel having the current threshold may be categorized into amplitude bin k (defined by amplitude range [I(k−1), I(k)], if $I(k-1) \leq I_{th}(i) < I(k)$. After voxel categorization, at least some of the amplitude bins may each include a set of the 3D voxels.

The amplitude effect calculator 1024 may compute, for each of the amplitude bins that includes the 3D voxels, a respective amplitude effect using a sum of voxel metric effect of the 3D voxels in that amplitude bin. For example, for j-th amplitude bin that contains N categorized voxels with respective voxel metric effect $X_j(1), X_j(2), \ldots, X_j(N)$, the amplitude effect Y(j) may be determined using Equation (4) as follows:

$$Y(j) = X_j(1) + X_j(2) + \ldots + X_j(N) \quad (4)$$

In some examples, voxel categorization into different amplitude bins and computation of amplitude effect for each amplitude bin may be performed concurrently, such that the amplitude effector calculator 1024 computes for each amplitude bin a running total of all the voxels effects as they are categorized. The accumulator 1026 may generate the metric value (MV) adaptively by accumulating the amplitude effects of the ordered amplitude bins starting from the beginning of the ordered amplitude bins with the lowest amplitude range. For example, the accumulation at (j+1)-th iteration may include the amplitude effect Y(j+1) representing a contribution of the 3D voxels in the (j+1)-th amplitude bin. The accumulation may be represented by the following equation:

$$MV(j+1) = MV(j) + Y(j+1) \quad (5)$$

The amplitude effect Y is a signed number. As such, the accumulated metric value after each iteration may be greater or less than the accumulated metric value before that iteration. The terminal amplitude bin identifier 1028 may evaluate the accumulated MV at each iteration, and to identify a terminal amplitude bin corresponding to an accumulated MV meeting a specified criterion. The terminal amplitude bin has a corresponding amplitude effect Y(n). In an example, the terminal amplitude bin may be identified when an inclusion of Y(n) would result in a decrease of the accumulated metric value exceeding a specified tolerance, that is, $MV(n) < MV(n-1)$ and $MV(n-1) - MV(n) > \delta$. The terminal amplitude bin identifier 1028 may determine, for the specific stimulation location or current fractionalization, the best metric $MV_{opt}$ to be the adaptively generated metric value MV(n), and the lowest stimulation current $I_{min}$ to be a representative amplitude determined from the identified terminal amplitude bin. In an example, the $I_{min}$ may be determined as a median amplitude of the terminal amplitude bin.

The $MV_{opt}$ and the associated $I_{min}$ for a specific stimulation location, as determined by the metric value optimization circuit 1010 or 1020, may be provided to the stimulation location circuit 928 to determine an optimal coordinates, as discussed above with reference to FIG. 9. Additionally or alternatively, the $MV_{opt}$ and the associated $I_{min}$ may be stored in the external storage device 830, or displayed on a display screen of the user interface 810.

The metric value optimization circuits 1010 and 1020 as discussed herein each may improve the efficiency and accuracy of searching for a lowest stimulation current $I_{min}$ associated with the best metric value $MV_{opt}$. The amplitude search space may be large (e.g., over 100 amplitude steps), and a complete search may lye time-consuming. Therefore, there is a need for systems and methods to perform complete search to quickly determine the lowest stimulation current $I_{min}$. Conventionally, $I_{min}$ may be identified using either an exhaustive search or a binary search. For a 3D voxelized tissue model comprising m voxels, and an amplitude search space comprising n candidate discrete amplitudes, the running time or execution steps for an exhaustive search grows at the order of m*n, that is, O(m*n). A binary search of the amplitude space following a metric gradient to determine $I_{min}$ may require a running time of O(m*log(n)). Additionally, the conventional methods require a tradeoff of speed versus the possibility of missing features due to the non-monotonic nature of the metric. The amplitude search methods as implemented in the metric value optimization circuits 1010 and 1020 involve complete amplitude search, yet in faster time. For example, the voxel metric effect-based search in the metric value optimization circuits 1010 requires running time in the order of O(m*log(m)), while the amplitude effect-based search in the metric value optimization circuits 1020 provides complete search of the amplitude space with running time of O(m). Therefore, the metric value optimization circuits 1010 and 1020 and the corresponding methods discussed herein may substantially reduce the time taken to determine $I_{min}$.

Figure 11:
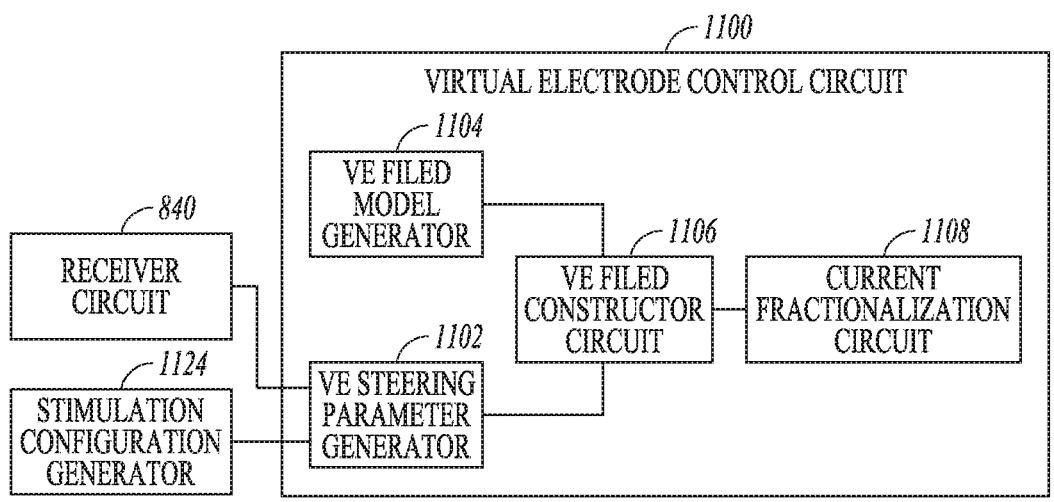
FIG. 11 illustrates an example of a virtual electrode control circuit for steering a virtual electrode on a graphical user interface.

FIG. 11 illustrates, by way of example and not limitation, an embodiment of a virtual electrode control circuit 1110 configured to steer a virtual electrode (VE) on a graphical user interface (GUI). A VE is a simplified representation of one electrode or an array of electrodes, rather than a scaled depiction of an electrode with geometric or physical properties such as actual size, shape, spread, dimension, position or orientation with respect to the lead body, or inter-electrode spacing, among others. In an example, a VE of a stereotyped shape may be tied to a specific real electrode configuration pre-loaded onto a device memory. The VE control circuit 1110 enables a user to manipulate the VE via the GUI, including moving the VE along the longitudinal axis of the lead, rotate the VE on the angular axis, or change the size or spread of the VE. Those dimensions over which the electrodes cannot be expanded or move about may be identified on the GUI and made un-adjustable by the user via a display of other means. If multiple VEs are presented, the GUI is enabled such that a user may select or toggle the VEs.

The virtual electrode control circuit 1110 may be part of external control circuitry in the external programming device 802. As illustrated in FIG. 11, the virtual electrode control circuit 1110 may include one or more of a VE steering parameter generator 1102, a VE field model generator 1104, a VE field constructor circuit 1106, and a current fractionalization circuit 1108. The VE steering parameter generator 1102 may be coupled to the stimulation configuration generator 1124 and the receiver circuit 840, and configured to generate one or more VE steering parameters, including VE type, VE location, VE size and spread, among others. The stimulation configuration circuit 1124 may be an embodiment of the stimulation configuration generator circuit 824 or 924. In an example, the VE location may include an optimal longitudinal-angular coordinate pair $(Z_{opt}, \theta_{opt})$ that corresponds to the best metric value $MV_{opt}$ at a lowest stimulation current $I_{min}$, such as produced by the stimulation location circuit 928. The lowest stimulation current $I_{min}$ may be determined using the voxel metric effect-based amplitude search as previously discussed with reference to FIG. 10A, or the amplitude effect-based amplitude search as previously discussed with reference to FIG. 10B. In various examples, the VE steeling parameters may alternatively be provided by a user, or received from an external storage device via the receiver circuit 840. A user may modify one or more previously generated VE steering parameters, such as a VE location.

Figure 12A:
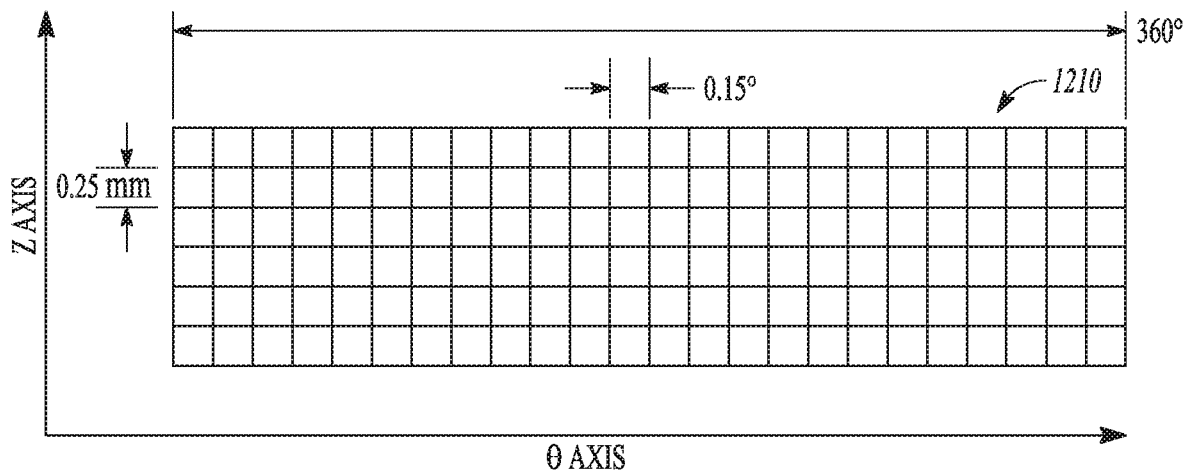
FIGS. 12A-12C illustrate examples of virtual electrode representations and electrode primitives designated as an anode or a cathode.

The VE field model generator 1104 may be configured to generate a VE field model. In an example, the VE field model may be represented by a closed-form representation (e.g., an equation) describing the VE. In another example, the VE field model may include representations of a plurality of electrode primitives each having respective size, shape, location, and primitive voltage field ($V_P$). Referring now to FIG. 12A, which illustrates, by way of example and not limitation, a two-dimensional (2D) grid 1210, representing a three-dimensional (3D) VE surface, which is designated for primitive electrode placement. The 2D grid 1210 has a longitudinal coordinate (along the Z-axis) and an angular coordinate (along the θ-axis). The longitudinal coordinate represents an offset from a reference point on a lead (e.g., electrode center) along the length of the lead. The angular coordinate represents a rotation angles between 0 and 360°. In the illustrated example, the grid has a size of 0.25 mm along the Z-axis and a rotation angle of 15° along the θ-axis. As a result, a VE that represents a ring electrode may have 360°/15°=24 directional grids over a circumference of the VE. The 2D grid 1210 as shown in FIG. 12A may extend as needed in the Z-axis.

Figure 12B:
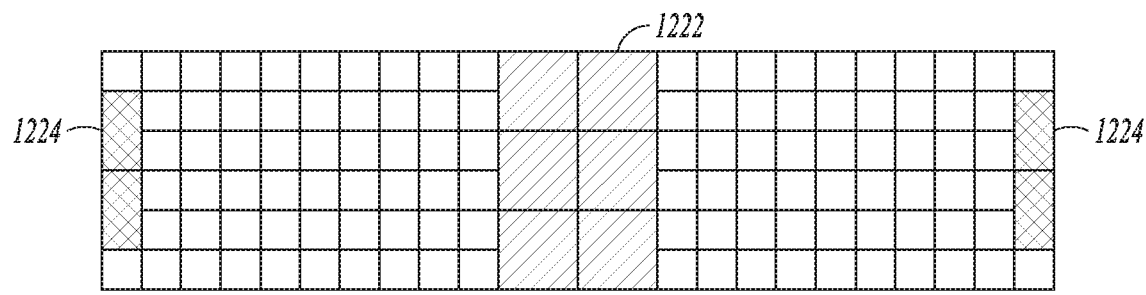
Figure 12C:
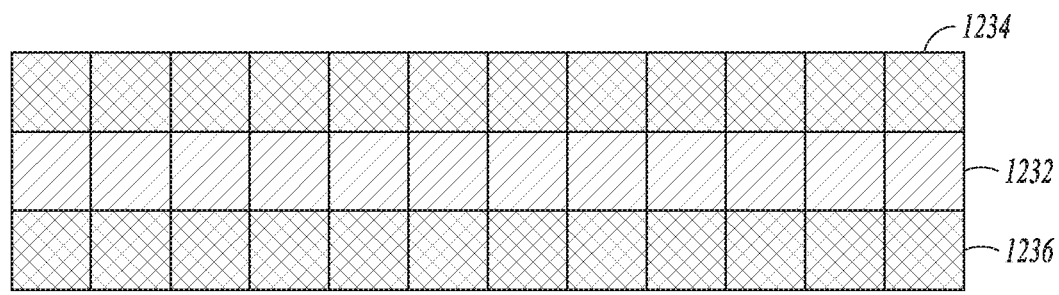

FIGS. 12B-12C illustrate examples of electrode placement to construct particular virtual electrodes. The virtual electrode may be designated as an anode or a cathode. In an example, electrode primitives may be defined as having a size of 0.5 mm by 30°. In another example, the electrode primitive may have a size of 1.5 mm by 90°. The electrode primitives may each be assigned respective primitive weight factors. The primitive weight factor represents the polarity and relative amount of current distribution to the primitive. The weight factor is a non-zero scalar between −1 and 1, where a positive weight represents an electrode primitive being used an anode, and a negative weight represents an electrode primitive being used a cathode. As illustrated in FIG. 12B, a cluster 1222 of six electrode primitives, each having a primitive size of 0.5 mms by 30°, are respectively assigned a negative weight ($-1 \leq w < 0$). A cluster 1224 of two electrode primitives, each having a primitive size of 0.5 mms by 30°, are respectively assigned a negative weight ($0 < w \leq 1$). Therefore, the cluster 1222 is designated as a cathode, and the cluster 1224 is designed at an anode. The cathode and the anode are spatially opposite to each other on a circumference of the VE. In the example illustrate in FIG. 12C, a cluster 1232 of primitives span an entirety of a circumference of the VE (0-360°), and are assigned a negative weight. Two clusters 1234 and 1236 of primitives each also span an entirety of a circumference of the VE, and are assigned a positive weight. Therefore, the cluster 1232 represents a ring electrode for use as a cathode, and the clusters 1234 and 1236 each represent a ring electrode for use as an anode.

Returning now to FIG. 11, the VE filed constructor circuit 1106 may construct a voltage field ($V_{VE}$) of the virtual electrode using superposition of the primitive voltage field ($V_P$) of each of the plurality of electrode primitives. In an example, the $V_{VE}$ may be constructed using a weighted combination of voltage field ($V_p$) of the electrode primitives. The $V_P$'s may be scaled by their respective primitive weight factors, that is, $V_{VE} = \Sigma w(i) * V_P(i)$, where i denotes an index of an electrode primitive, w(i) denotes the signed primitive weight factor for electrode primitive having a primitive voltage field $V_P(i)$.

In various examples, the VE filed constructor circuit 1106 may be further configured to estimate a threshold current using the constructed VE voltage field $V_{VE}$. The threshold current represents a minimum current required for modulating a physiologic target, such as a neural target including one or more of an axon, a cell body, an axon hillock, a synapse, a branch, or connective tissue like neuroglia, among other targets within the voltage field of the virtual electrode. Desired modulation of the physiologic target may include action potential generation, firing rate modulation, activation inhibition, or other target modeling criteria. In an example, a machine-learning method may be used for estimation. This takes the voltages along a fiber and calculates a set of predictor values, then uses the predictor values to determine the fiber current threshold. Examples of the machine-learning method may include genetic algorithm, fuzzy logic, particle swarm, simulated annealing, or gradient descent, among others. In another example, the threshold current may be estimated analytically using a current-distance curve that is based on a rheobase current and the distance between a target element and the virtual electrode. In some examples, the threshold current may be estimated based on computational models such as Hodgkin-Huxley cable model or some variant thereof. In some examples, the threshold current and the $V_{VE}$, for a given lead type may be pre-calculated and stored in a storage device, such as in a lookup table or other data structure. The VE filed constructor circuit 1106 may perform a lookup search for the threshold current that corresponds to the constructed YE voltage field $V_{VE}$. In some examples, a user may specify a cost function based on a desired balance between therapeutic efficacy and side effect produced by the voltage field WE, and adjust the threshold current accordingly to optimize the cost function.

The current fractionalization circuit 1108 may fractionalization of electrical current across a plurality of electrodes based on the location of the virtual electrode relative to the plurality of electrodes. In an example, the current fractionalization circuit 1108 may convert the voltage field ($V_{VE}$) of the virtual electrode to a voltage field of the plurality of electrodes using regression fitting, such as a linear or nonlinear regression model. In an example, the conversion may involve a least-square field fitting of $V_{VE}$.

The current fractionalization circuit 1108 may determine the fractionalization of the real electrodes based on the location of the VE relative to the real electrodes. In an example, the real fractionalizations may be generated using percent overlap of the VE with a notional representation of the real electrodes. In numerous examples, the real fractionalizations may be generated using matrix inversion to match the combined fields of the real electrodes with the field of the virtual electrode, or using matrix inversion to match the i-th field of the real electrodes with the i-th virtual electrode.

In numerous examples, the stimulation configuration circuit 1124 may determine a lowest stimulation current $I_{min}$ that results in an optimal metric value under the electrical field generated by the virtual electrode ($V_{VE}$) with specific longitudinal and angular coordinates. The voltage field of the plurality of electrodes ($E_{AE}$), converted from $V_{VE}$, optionally along with the VE steering parameters and the lowest stimulation current $I_{min}$ corresponding to the optimal metric value, may be transmitted to the implantable stimulator 704 via the external telemetry circuit 852 and the wireless communication link 640. The implantable stimulator 704 may generate and deliver electrostimulation according to the voltage filed and other steering parameters. Additionally or alternatively, $E_{AE}$ and other steering parameters may be stored in the external storage device 830, or be displayed on a display screen of the user interface 810.

Figure 13:
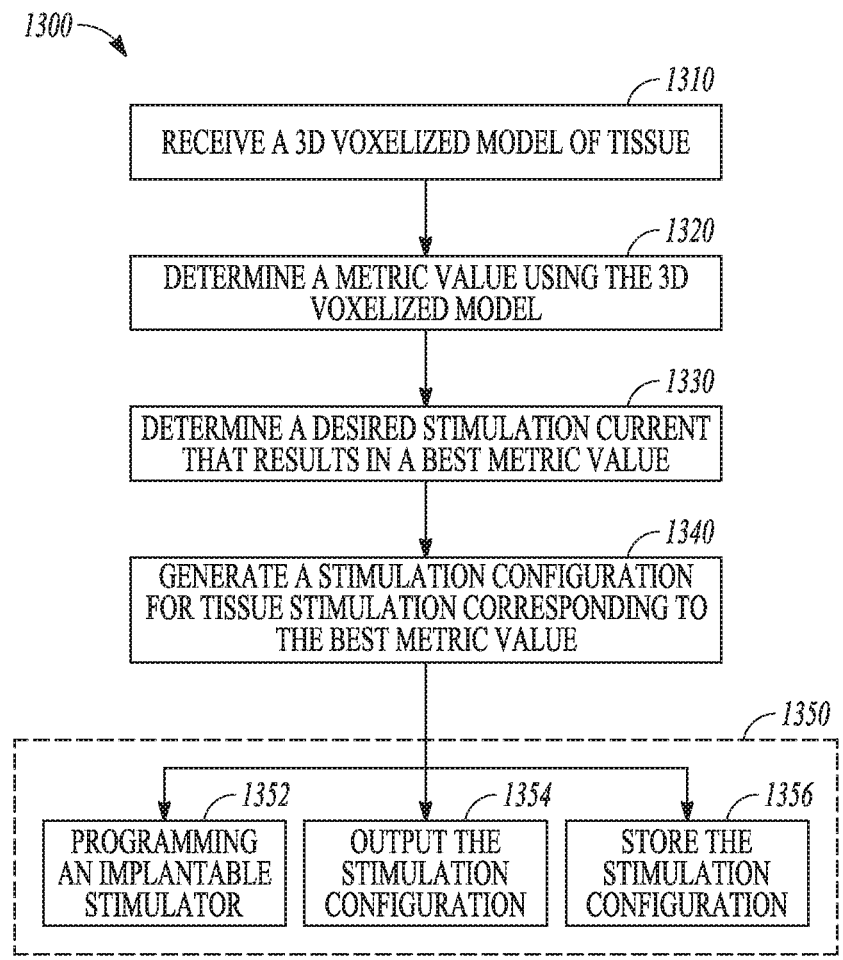
FIG. 13 illustrates an example of a method for controlling delivery of electrostimulation to specific tissue of a patient via an external programming device.

FIG. 13 illustrates, by way of example and not limitation, a method 1300 for controlling delivery of electrostimulation to specific tissue of a patient, such as BBS, SCS, PNS, VNS, or other types of neurostimulation, via an external programming device. The method 1300 may be implemented in an external device, such as one of the external programming devices 102, 302, or 802, and used to program an implantable device, such as the stimulator 704 or one of the IPGs 404, 504, or 604. In an example, at least a portion of the method 1300 may be implemented and executed by the CP 630 and/or the RC 632.

The method 1300 begins at step 1310, where a 3D voxelized model of tissue may be received. The 3D voxelized model may comprise an array of 3D voxels. Each voxel has a voxel volume and a voxel value. Each voxel may be specified as belonging to one of a plurality of regions, such as a target region or an avoidance region. The regions may each be assigned a corresponding weight factor w signifying the relative significance of the clinical outcome. A target region may be associated with a positive weight factor, and an avoidance region may be associated with a negative weight factor. In some examples, the 3D voxelized model may be constructed from a 3D triangulated surface representation of the tissue, such as by using linear or non-linear interpolation of the complex geometry of the 3D triangulated surface.

At 1320, a metric value (MV) and current fractionalization may be determined using the 3D voxelized model. The MV represents a clinical effect of electrostimulation on the region according to a specific stimulation current and a specific fractionalization of electrical current across the plurality of electrodes. The MV may be computed by accumulating the voxel effects (also known as voxel contributions to the MV) of all the voxels in the 3D voxelized model, such as according to Equations (1) and (2) as previously discussed.

At 1330, a first stimulation current that results in a best metric value ($MV_{opt}$) may be determined. The first stimulation current may be characterized by amplitude, energy, or other intensity descriptors of the stimulation current, or pulse width, pulse rate, waveform morphology or pattern of the stimulation current. The $MV_{opt}$ is a matric value satisfying a clinical effect condition, such as exceeding a threshold metric value $MV_{TH}$, or meets a specified optimization criterion. In an example, the $MV_{opt}$ is the largest MV under a specific electrical current fractionalization. The first stimulation current may be determined as a minimal stimulation current ($I_{min}$) that results in the $MV_{opt}$. Also at 1330 a specific current fractionalization $F_I^*$ associated with the $MV_{opt}$ may be determined.

At 1340, a stimulation configuration for tissue stimulation may be generated, such as via the stimulation configuration generator 824. The stimulation configuration may include the first stimulation current, such as $I_{min}$, and information about the current fractionalization $F_I^*$ associated with the $MV_{opt}$. Examples of determining the $I_{min}$ that results in the best metric value $MV_{opt}$ under a specified electrical current fractionalization $F_I$ are discussed below, such as with reference to FIGS. 15A-15B.

The stimulation configuration, including the $I_{min}$ and $F_I^*$ associated with the $MV_{opt}$ among other programming parameters, may be output to a user or a process at 1350. In an example, at 1352, the stimulation configuration may be transmitted to an implantable device, such as the implantable stimulator 704, via a communication link such as the wireless communication link 640. Electrostimulation such as DBS may be generated by the implantable device and delivered to target tissue according to the stimulation configuration. The programming of the implantable device using the stimulation configuration may be carried out automatically or triggered by a user command or a specific event. In another example, at 1354, the stimulation configuration may be presented to a user (e.g., a clinician or a patient), such as being displayed on a display screen of the user interface 810. The user may adjust the stimulation configuration through the user interface 810. In yet another example, at 1356, the stimulation configuration may be stored in a storage device, such as the storage device 830 in the external programming device. Other stimulation programming parameters, such as stimulation waveforms, stimulation electrode configurations, and stimulation fields, may also be stored in the storage device.

Figure 14:
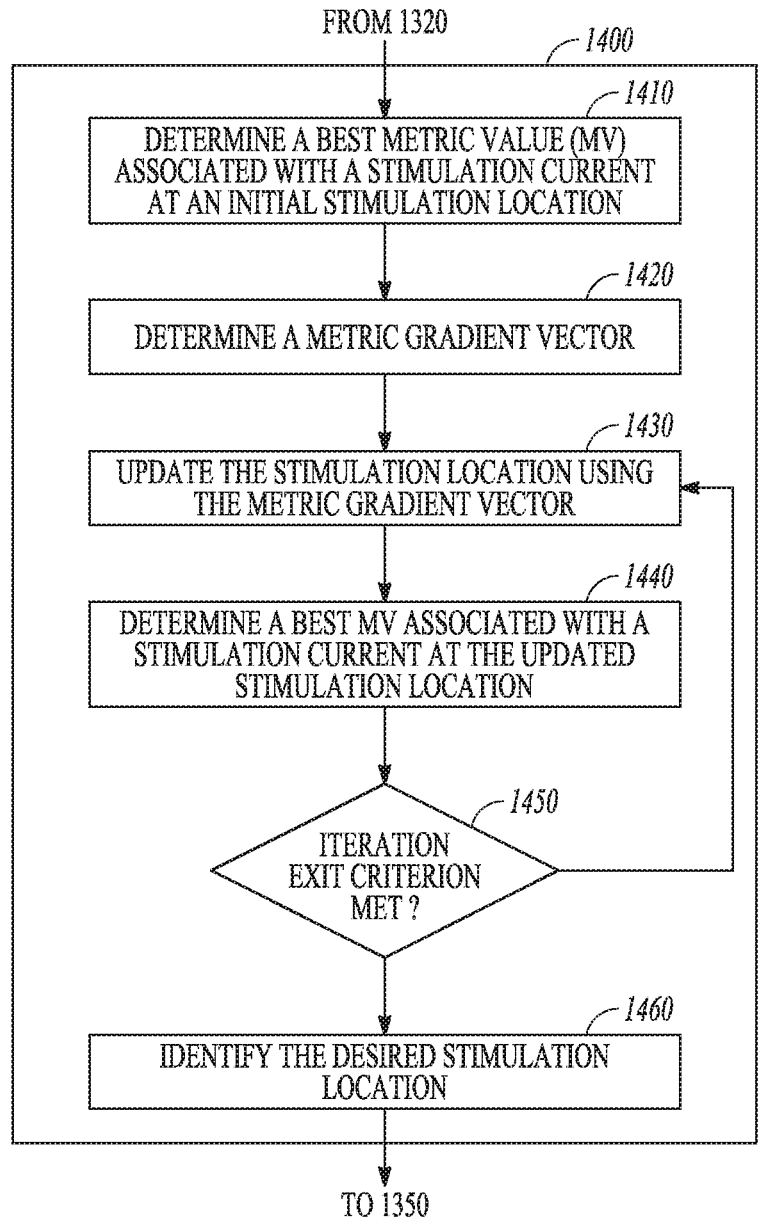
FIG. 14 illustrates an example of a method for identifying a desired stimulation location with respect to positions of the plurality of electrodes.

FIG. 14 illustrates, by way of example and not limitation, a method 1400 for identifying a desired stimulation location with respect to positions of the plurality of electrodes. The desired stimulation location may be a stimulation parameter included in the stimulation configuration. The method 1400 is an embodiment of stimulation configuration generation at step 1330-1340 of the method 1300, and may be implemented and executed by the stimulation configuration generator circuit 924.

The desired stimulation location corresponds to the best metric value and its associated stimulation current. The desired stimulation location may be represented by coordinates of a virtual electrode in a coordinate space, including at least a longitudinal coordinate (Z) and an angular coordinate (θ). In an example, the longitudinal and angular coordinates may be represented by offsets ($Z_d$, $\theta_d$) relative to the reference electrode positions ($Z_0$, $\theta_0$). The method 1400 uses gradient descent to search for the desired stimulation location ($Z_{opt}$, $\theta_{opt}$) that maximizes the metric value. The search may be carried out in a subspace defined by $Z_d$ and $\theta_d$ within their respective ranges, such as $Z_{d\text{-}min} \leq Z_d \leq Z_{d\text{-}max}$ and $0 \leq \theta_d < 360°$.

At 1410, given an initial stimulation location, an initial best metric value $MV_{opt}(0)$ corresponding to a smallest stimulation current $I_{min}(0)$ may be computed. The initial stimulation location includes initial coordinates ($Z_d(0)$, $\theta_d(0)$). In an example, the $MV_{opt}$ may be determined using voxel ranking or amplitude ranking, such as to be discussed in the following with reference to FIGS. 15A-15B. At 1420, a metric gradient vector ($\nabla M_{P1P2P3}$) is determined using a 3D triangulated surface spanned by three points (P1, P2, P3) in the coordinate space. The metric gradient vector points to a direction of increase in the metric value. At 1430, the initial coordinates ($Z_d(0)$, $\theta_d(0)$) may be updated to ($Z_d(1)$, $\theta_d(1)$) using the metric gradient vector $\nabla M_{P1P2P3}$. Accordingly, at 1440, a new best metric value $MV_{opt}(1)$ corresponding to a smallest stimulation current $I_{min}(1)$ may then be determined at the new coordinates ($Z_d(1)$, $\theta_d(1)$). Like the $MV_{opt}(0)$ at 1410, the $MV_{opt}(1)$ at 1440 may be computed using voxel ranking or amplitude ranking, the details of which are discussed with reference to FIGS. 15A-15B.

At 1450, a specific iteration exit criterion is checked to determine whether the search process may be terminated. In one example, the exit criterion includes an MV convergence criterion. For example, the search process may stop when the difference between the best metric values before and after present iteration falls below a threshold. In another example, the search process may stop if coordinate update has reached a specified maximum number of iterations. In yet another example, the exit criterion may include a coordinate convergence criterion, such as when a difference between the coordinate pairs before and after present iteration falls below a threshold.

If the iteration exit criterion is not met at 1450, the search process continues at 1430, where a new metric gradient vector may be computed, and the stimulation location may be updated using the new metric gradient vector. The new metric gradient vector may be computed based on a 3D triangulated surface spanned by three points including a point (Q) along the direction of the determined metric gradient vector, and two points (Px, Py) selected from the three points (P1, P2, P3) that are closer to the point Q. However, if at 1450 the iteration exit criterion has been met, then at 1460 the lowest stimulation current $I_{min}$ that corresponds to the $MV_{opt}$ may be determined. The desired stimulation location may be identified as the coordinate pair ($Z_{opt}$, $\theta_{opt}$) corresponding to the best metric value $MV_{opt}$. A stimulation state, including information about the optimal coordinate pair ($Z_{opt}$, $\theta_{opt}$) and the lowest stimulation current $I_{min}$, may be output to a user or a process at 1350. For example, the stimulation state may be stored in the external storage device 830, displayed on a display screen of the user interface 810, or transmitted to an implantable stimulator to program an electrostimulation therapy.

Figure 15A:
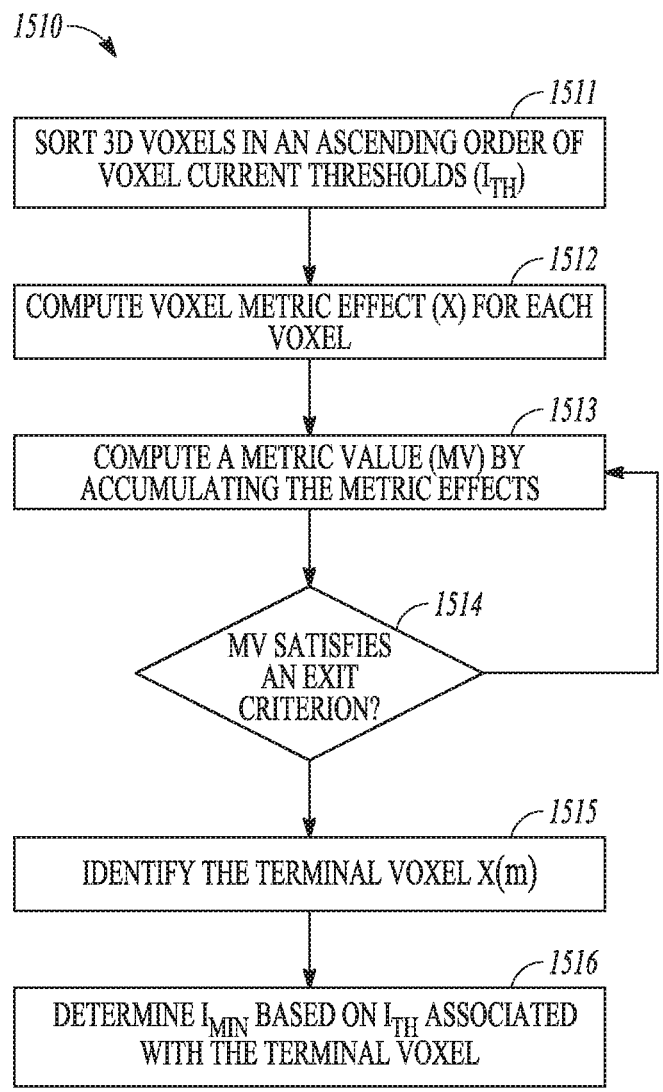
FIGS. 15A-15B illustrate examples of methods for determining the best metric value for a fractionalization or specified stimulation location, and the lowest stimulation current that generates that metric.
Figure 15B:
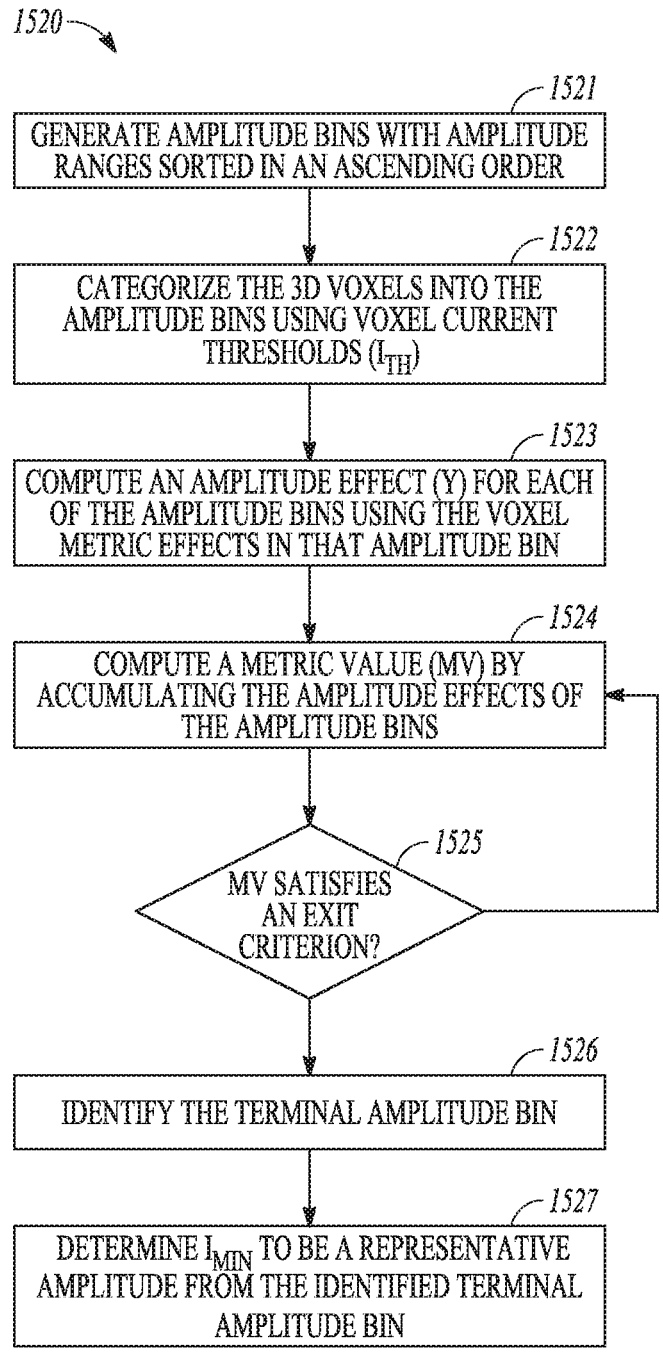

FIGS. 15A-15B illustrate, by way of example and not limitation, methods 1510 and 1520 for determining the best metric value $MV_{opt}$ for a fractionalization $F_I$ or specified stimulation location, and the lowest stimulation current $I_{min}$ that generates that metric. The methods 1510 and 1520 are embodiments of steps 1410 or 1440 of the method 1400 for determining the best metric value $MV_{opt}$ associated with a smallest stimulation current $I_{min}$.

The method 1510, as illustrated in FIG. 15A, may be implemented and executed by the metric value optimization circuit 1010. The method 1510 commences at step 1511, where 3D voxels in a 3D voxelized tissue model are sorted in an ascending order of voxel current threshold $I_{th}$. The $I_{th}$ may be received from a system user such as via the receiver circuit 840, or generated based on the specified current fractionalization. At 1512, a voxel metric effect may be computed for each of the 3D voxels using voxel volume, voxel value, and weight factor associated with the structure or region to which the voxel belongs, such as according to Equation (1). Then, starting from the 3D voxel with the lowest voxel current threshold $I_{th}$, a metric value (MV) may be generated at 1513 by accumulating the voxel metric effects as the sorted voxels are walked in smallest to largest $I_{th}$ order, such as according to Equation (3). At 1514, the accumulated MV at each iteration may be compared to a specific criterion. If the accumulated MV meets the exit criterion at 1514, such that an inclusion of X(m) would result in a decrease of the presently accumulated MV, and the amount of decrease exceeds a specified tolerance (i.e., MV(m)<MV(m−1) and MV(m−1)−MV(m)>δ), then the iterative search process may stop, and a terminal voxel may be identified at 1515. However, if the accumulated MV does not meet the exit criterion, then the MV accumulation process may continue by including the voxel metric effect of another voxel from the sorted voxel list.

At 1516, for the specific stimulation location or current fractionalization, the best metric $MV_{opt}$ may be determined to be the adaptively generated metric value MV(m), and the lowest stimulation current $I_{min}$ may be determined using the current threshold $I_{th}(m)$ associated with the identified terminal voxel. In an example, the lowest stimulation current $I_{min}$ may be determined as the smallest amplitude step that is greater than or equal to the current threshold $I_{th}(m)$ associated with the identified terminal voxel. The best metric $MV_{opt}$ and the lowest stimulation current $I_{min}$ may be returned and used by the method 1400, or output to a user or a process at 1350 of the method 1300.

The method 1520, as illustrated in FIG. 15B, may be implemented and executed by the metric value optimization circuit 1020. The method 1520 commences at step 1521, where a specified stimulation current amplitude range 0-20.0 mA) may be discretized into different amplitude bins each including respective amplitude ranges. The amplitude ranges of the amplitude bins may be non-overlapping. The amplitude bins may be arranged in an ascending order of the amplitude. At 1522, each of the 3D voxels may be assigned to one of the amplitude bins based on the respective voxel current threshold ($I_{th}$) for a specific current fractionalization. For example, a 3D voxel having the current threshold $I_{th}(i)$ may be assigned to amplitude bin k (defined by amplitude range [I(k−1), I(k)], if I(k−1)≤$I_{th}(i)$<I(k). The amplitude bins thus may each include a number of 3D voxels. At 1523, for each of the amplitude bins that includes the 3D voxels, a respective amplitude effect Y may be computed by adding up the voxel metric effect of the categorized 3D voxels in that amplitude bin, such as according to Equation (4).

A metric value (MV) may be computed at 1524 by accumulating the amplitude effects of the ordered amplitude bins starting from the amplitude bines the lower amplitude ranges, such as according to Equation (5). At 1525, the accumulated MV at each iteration may be compared to a specific criterion. If the accumulated MV meets the exit criterion, such that an inclusion of Y(n) would result in a decrease of the accumulated MV that exceeds a specified tolerance, then the iterative search process may stop, and a terminal amplitude bin may be identified at 1526. However, if the accumulated MV does not meet the exit criterion, then the MV accumulation process may continue by including the amplitude effect of another amplitude bin from the sorted bin list.

At 1527, for the specific stimulation location or current fractionalization, the best metric $MV_{opt}$ may be determined to be the adaptively generated metric value MV(n), and the lowest stimulation current $I_{min}$ may be determined as a representative amplitude determined from the identified terminal amplitude bin. In an example, the $I_{min}$ may be determined as the median amplitude of terminal amplitude bin. The best metric $MV_{opt}$ and the lowest stimulation current $I_{min}$ may be returned and used by the method 1400, or output to a user or a process at 1350 of the method 1300.

Figure 16:
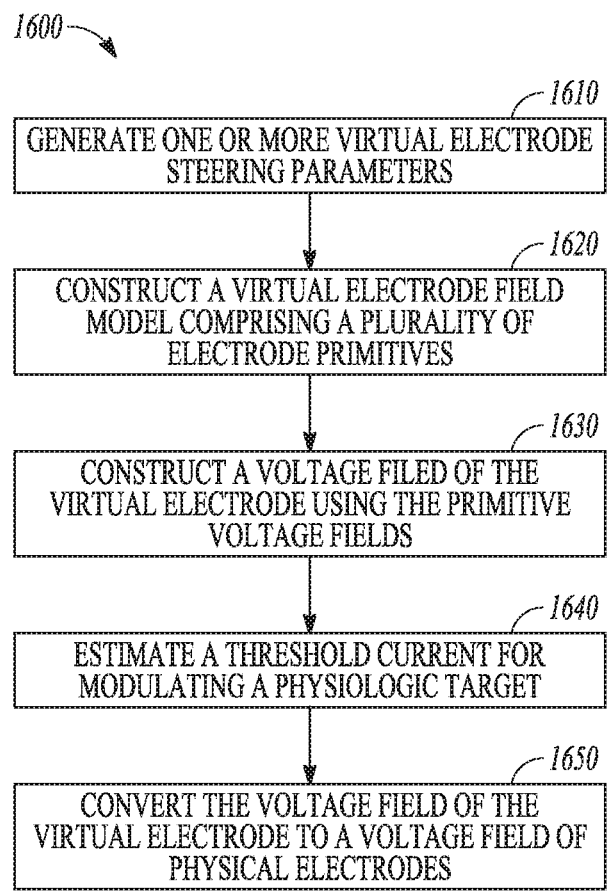
FIG. 16 illustrates an example of a method for using electrode primitives, a virtual electrode, and steering coordinates to generate a real electrode fractionalization.

FIG. 16 illustrates, by way of example and not limitation, a method 1600 for using electrode primitives, a virtual electrode, and steering coordinates to generate a real electrode fractionalization. As previously discussed, a VE is a simplified representation of one electrode or an array of electrodes. The method 1600 may be implemented and executed by the virtual electrode control circuit 1100.

The method 1600 begins at step 1610, where one or more VE steering parameters may be generated. Examples of the VE parameters may include VE type, VE location, VE size and spread, among others. The VE location may include an optimal longitudinal-angular coordinate pair $(Z_{opt}, \theta_{opt})$ that corresponds to the best metric value $MV_{opt}$ at a lowest stimulation current $I_{min}$, such as produced using the method 1400. The lowest stimulation current $I_{min}$ may be determined using the voxel metric effect-based amplitude search, such as that discussed in FIGS. 15A-15B.

At 1620, a VE field model may be constructed, such as using the VE field model generator 1104. The VE field model comprises a plurality of electrode primitives each having respective size, shape, location, and primitive voltage field $(V_P)$. The electrode primitives may be defined using the 2D grid, such as illustrated in FIGS. 12A-12C. The electrode primitives may each be assigned respective primitive weight factors representing the polarity (i.e., as an anode or a cathode) and relative amount of current distributed at the primitive.

At 1630, a voltage field $(V_{VE})$ of the virtual electrode may be constructed using the primitive voltage field $(V_P)$ of each of the plurality of electrode primitives. In an example, the voltage field $V_{VE}$ may be constructed using superposition of the electrode primitive voltage fields. In an example, the voltage field $V_{VE}$ may be constructed using weighted sum of the electrode primitive voltage fields, represented by $V_{VE} = \Sigma w(i) * V_P(i)$, where i denotes an index of an electrode primitive, denotes the signed primitive weight factor for electrode primitive having a primitive voltage field $V_P(i)$.

At 1640, the constructed VE voltage field $V_{VE}$ may be used to estimate a threshold current representing a minimum current required to modulate a physiologic target, such as a neural target including one or more of an axon, a cell body, an axon hillock, a synapse, a branch, or connective tissue like neuroglia, among other targets within the voltage field of the virtual electrode. Desired modulation of the physiologic target may include action potential generation, firing rate modulation, activation inhibition, or other target modeling criteria. A user may adjust the voltage field such as by translating and/or rotating the VE according various current steering parameters. In an example, the threshold current may be estimated using a computational model (e.g., Hodgkin-Huxley cable model or a variant thereof), or based on a machine-learning method such as genetic algorithm, fuzzy logic, particle swarm, simulated annealing, or gradient descent, among others. In another example, the threshold current may be estimated analytically using a current-distance curve that is based on a rheobase current and the distance between a target element and the virtual electrode.

In some examples, the threshold current and the $V_{VE}$ for a given lead type may be pre-calculated and stored in a storage device, such as in a lookup table or other data structure. The threshold current may be pre-calculated for a multitude of electrode locations such represented by longitudinal (Z) and angular ($\theta$) locations, where Z takes values between a minimum and a maximum defined by the lead type, and $\theta$ takes values between 0 and 360°. The lookup table may be created using least squares voltage field fitting to determine the optimal real electrode fractionalization for various VE voltage field values at different (Z, $\theta$) locations. A lookup search may be performed at 1640 to identify the threshold current that corresponds to the constructed YE voltage field $V_{VE}$. In some examples, a user may specify a cost function based on a desired balance between therapeutic efficacy and side effect produced by the voltage field $V_{VE}$, and adjust the threshold current accordingly to optimize the cost function.

At 1650, electrical current fractionalization across the plurality of electrodes may be determined based on the location of the virtual electrode relative to the plurality of electrodes. The current fractionalization estimation may involve a process of converting the voltage field of the virtual electrode $(V_{VE})$ to a voltage field of the plurality of electrodes. In an example, the conversion is carried out using regression fitting, such as a linear or nonlinear regression model. An example of the regression model includes a least-square regression. The fractionalizations may be generated using percent overlap of the VE with a notional representation of the real electrodes. In various examples, the fractionalizations may be generated using matrix inversion technique to match the combined fields of the real electrodes with the field of the virtual electrode, or to match a field of a particular real electrode (e.g., the i-th field) with a particular virtual electrode (e.g., the i-th virtual electrode). In various examples, the fractionalizations may be rounded, and the total of the absolute anodic and cathodic fractionalization values may be summed. If a summed fractionalization value (for either anodic or cathodic fractionalization) is larger than 100, then the fractionalization may be normalized or otherwise fixed such that said fractionalization adds to 100. The fixed anodic and cathodic fractionalization may then be programmed to the real electrodes, or presented to a user (e.g., clinician).

Figure 17:
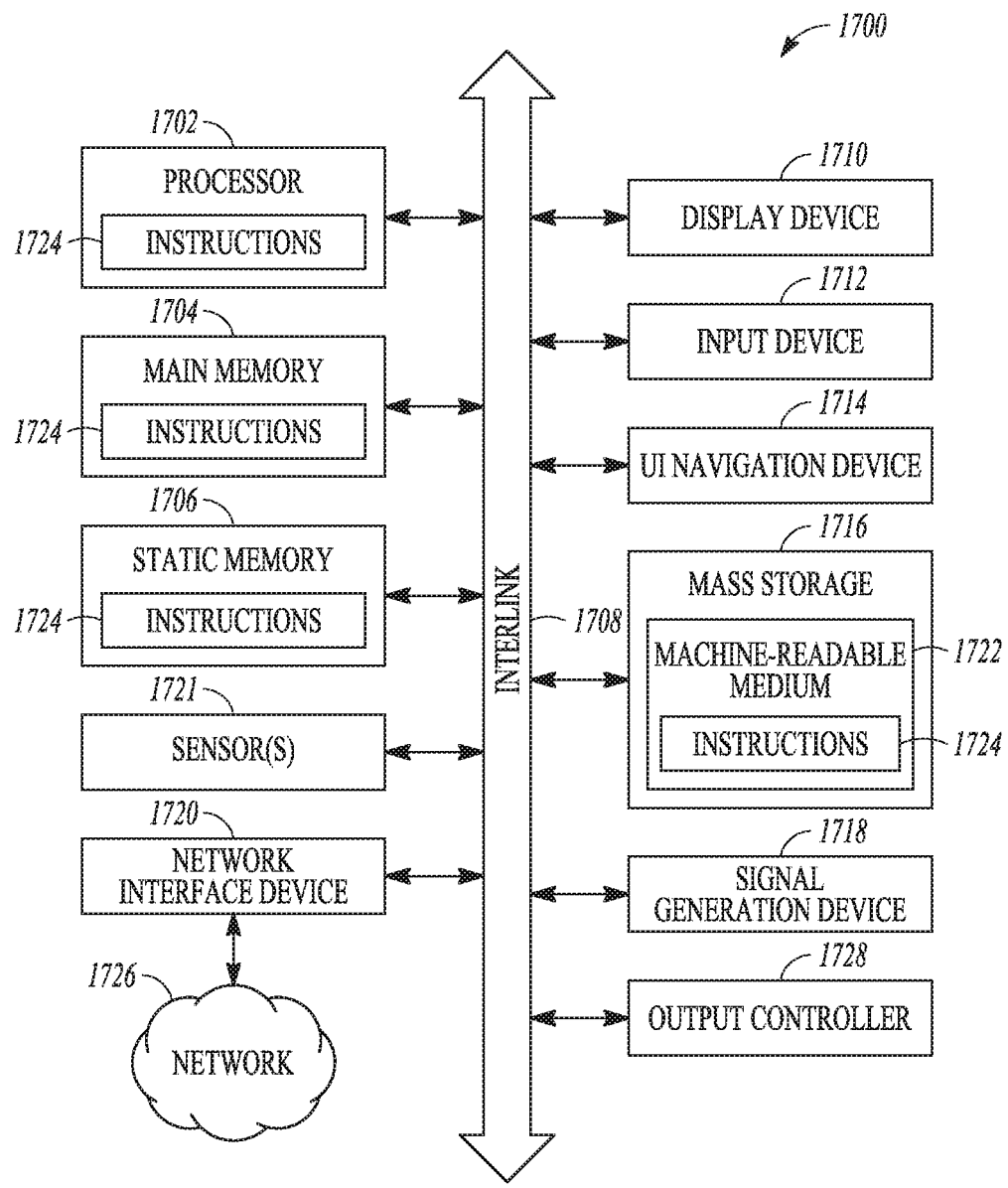
FIG. 17 illustrates a block diagram of an example machine upon which any one or more of the techniques (e.g., methodologies) discussed herein may perform.

FIG. 17 illustrates generally a block diagram of an example machine 1700 upon which any one or more of the techniques (e.g., methodologies) discussed herein may perform. Portions of this description may apply to the computing framework of various portions of the LCP device, the IMD, or the external programmer.

In alternative embodiments, the machine 1700 may operate as a standalone device or may be connected (e.g., networked) to other machines. In a networked deployment, the machine 1700 may operate in the capacity of a server machine, a client machine, or both in server-client network environments. In an example, the machine 1700 may act as a peer machine in peer-to-peer (P2P) (or other distributed) network environment. The machine 1700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specific operations when operating. In an example, hardware of the circuit set may be immutably designed to carry out a specific operation (e.g., hardwired), in an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 1700 may include a hardware processor 1702 (e.g., a central processing unit (CPU), a graphics processing unit (GPU), a hardware processor core, or any combination thereof), a main memory 1704 and a static memory 1706, some or all of which may communicate with each other via an interlink (e.g., bus) 1708. The machine 1700 may further include a display unit 1710 (e.g., a raster display, vector display, holographic display, etc.), an alphanumeric input device 1712 (e.g., a keyboard), and a user interface (UI) navigation device 1714 (e.g., a mouse). In an example, the display unit 1710, input device 1712 and UI navigation device 1714 may be a touch screen display. The machine 1700 may additionally include a storage device (e.g., drive unit) 1716, a signal generation device 1718 (e.g., a speaker), a network interface device 1720, and one or more sensors 1721, such as a global positioning system (GPS) sensor, compass, accelerometer, or other sensors. The machine 1700 may include an output controller 1728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1716 may include a machine readable medium 1722 on which is stored one or more sets of data structures or instructions 1724 (e.g., software) embodying or utilized by any one or more of the techniques or functions described herein. The instructions 1724 may also reside, completely or at least partially, within the main memory 1704, within static memory 1706, or within the hardware processor 1702 during execution thereof by the machine 1700. In an example, one or any combination of the hardware processor 1702, the main memory 1704, the static memory 1706, or the storage device 1716 may constitute machine readable media.

While the machine readable medium 1722 is illustrated as a single medium, the term "machine readable medium" may include a single medium or multiple media (e.g., a centralized or distributed database, and/or associated caches and servers) configured to store the one or more instructions 1724.

The term "machine readable medium" may include any medium that is capable of storing, encoding, or carrying instructions for execution by the machine 1700 and that cause the machine 1700 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1724 may further be transmitted or received over a communications network 1726 using a transmission medium via the network interface device 1720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 1720 may include one or more physical jacks (e.g., Ethernet, coaxial, or phone jacks) or one or more antennas to connect to the communications network 1726. In an example, the network interface device 1720 may include a plurality of antennas to wirelessly communicate using at least one of single-input multiple-output (SINK)), multiple-input multiple-output (MIMO), or multiple-input single-output (MISO) techniques. The term "transmission medium" shall be taken to include any intangible medium that is capable of storing, encoding or carrying instructions for execution by the machine 1700, and includes digital or analog communications signals or other intangible medium to facilitate communication of such software.

Various embodiments are illustrated in the figures above. One or more features from one or more of these embodiments may be combined to form other embodiments.

The method examples described herein may be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like.

Such code may include computer readable instructions for performing various methods. The code may form portions of computer program products. Further, the code may be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for controlling delivery of electrostimulation to specific tissue of a patient, the system comprising:
a receiver circuit configured to receive a three-dimensional (3D) voxelized model of tissue representing a plurality of regions each specified as a target region or an avoidance region; and
control circuitry, including a stimulation programmer circuit configured to:
determine a metric value using the 3D voxelized model and a clinical effect of electrostimulation on the plurality of regions according to a stimulation current and a current fractionalization representing a distribution of the stimulation current across a plurality of electrodes;
execute an optimization process to search, in a coordinate space comprising a longitudinal coordinate and an angular coordinate, for a first metric value satisfying a clinical effect condition represented by a therapeutic benefit and a side effect of the electrostimulation, and to determine a first stimulation current corresponding to the first metric value; and
generate a stimulation configuration for tissue stimulation, the stimulation configuration including the first stimulation current and a current fractionalization corresponding to the first metric value; and
an electrostimulation circuit configured to generate and provide stimulation energy to the tissue according to the generated stimulation configuration.

2. The system of claim 1, wherein the electrostimulation circuit is included in an implantable stimulator, the system further comprising an external programming device configured to be communicatively coupled to the implantable stimulator,
the external programming device including the receiver circuit and the control circuitry.

3. The system of claim 1, wherein the search for the first metric value includes searching for a desired stimulation location with respect to positions of the plurality of electrodes,
wherein the desired stimulation location is represented by at least a longitudinal coordinate and an angular coordinate in the coordinate space, and corresponds to the first metric value and its associated stimulation current.

4. The system of claim 3, wherein the stimulation programmer circuit is configured to search for the longitudinal and angular coordinates that maximize the metric value.

5. The system of claim 4, wherein the stimulation programmer circuit is configured to iteratively search for the longitudinal and angular coordinates using a gradient-based method, and the stimulation programmer circuit is configured to determine a metric gradient vector using a 3D triangulated surface spanned by three points in the coordinate space, and to iteratively search for the longitudinal and angular coordinates using the metric gradient vector.

6. The system of claim 1, wherein the 3D voxelized model includes 3D voxels each having a voxel volume, and the stimulation programmer circuit is configured to determine the first metric value for a stimulation location using a combination of the voxel volumes of the 3D voxels each weighted by a weight factor,
wherein the weight factor is a positive scalar if the 3D voxel is situated in a target region, or a negative scalar if the voxel is situated in an avoidance region.

7. The system of claim 6, wherein the stimulation programmer circuit is configured to determine, for the stimulation location, a lowest stimulation current that results in the first metric value under the current fractionalization.

8. The system of claim 7, wherein the stimulation programmer circuit is configured to determine the lowest stimulation current using sorted 3D voxels in an ascending order of voxel current thresholds associated with the 3D voxels.

9. The system of claim 7, wherein the stimulation programmer circuit is configured to determine the lowest stimulation current using amplitude bins arranged in an ascending order of amplitude ranges, wherein the 3D voxels are each assigned to one of the amplitude bins based on respective voxel current thresholds associated with the 3D voxels.

10. The system of claim 1, wherein the stimulation configuration includes a virtual electrode state including one or more virtual electrode steering parameters, and wherein the control circuitry further includes a virtual electrode control circuit configured to steer a virtual electrode on a graphical user interface according to the one or more virtual electrode steering parameters.

11. The system of claim 10, wherein the virtual electrode comprises a plurality of electrode primitives each having respective primitive voltage fields, and
wherein the virtual electrode control circuit is configured to construct a voltage field of the virtual electrode using superposition of the primitive voltage fields of the plurality of electrode primitives each scaled by respective weight factors.

12. The system of claim 11, wherein the virtual electrode control circuit includes a current fractionalization circuit configured to convert the voltage field of the virtual electrode to a voltage field of the plurality of electrodes using regression fitting.

13. The system of claim 11, wherein the virtual electrode control circuit is further configured to estimate a threshold current using the voltage field of the virtual electrode, the threshold current representative of a minimum current required for modulating a physiologic target.

14. A method for controlling delivery of electrostimulation to specific tissue of a patient via an external programming device, the method comprising:
receiving a three-dimensional (3D) voxelized model of tissue via a receiver circuit, the 3D voxelized model representing a plurality of regions each specified as a target region or an avoidance region; and
determining, via a stimulation programmer circuit, a metric value using the 3D voxelized model and a clinical effect of electrostimulation on the plurality of regions according to a stimulation current and a current fractionalization representing a distribution of the stimulation current among a plurality of electrodes;
via the stimulation programmer circuit, executing an optimization process including searching, in a coordinate space comprising a longitudinal coordinate and an angular coordinate, for a first metric value satisfying a clinical effect condition represented by a therapeutic benefit and a side effect of the electrostimulation, and determining a first stimulation current corresponding to the first metric value; and generating a stimulation configuration for tissue stimulation via the stimulation programmer circuit, the stimulation configuration including the first stimulation current and a current fractionalization corresponding to the first metric value; and generating and providing stimulation energy to the tissue according to the generated stimulation configuration.

15. The method of claim 14, further comprising receiving a 3D triangulated surface representation of the tissue, and transforming the received 3D triangulated surface representation into the 3D voxelized model.

16. The method of claim 14, wherein searching for the first metric value includes searching for a desired stimulation location with respect to positions of the plurality of electrodes, the desired stimulation location represented by at least a longitudinal coordinate and an angular coordinate in the coordinate space, and corresponding to the first metric value and its associated stimulation current.

17. The method of claim 14, wherein the 3D voxelized model includes 3D voxels each having a voxel volume, and wherein determining the first metric value for a stimulation location includes using a combination of the voxel volumes of the 3D voxels each weighted by a weight factor, the weight factor being a positive scalar if the 3D voxel is situated in a target region, or a negative scalar if the voxel is situated in an avoidance region.

18. The method of claim 17, further comprising:
sorting the 3D voxels in an ascending order of voxel current thresholds associated with the 3D voxels, the voxel current thresholds each determined according to the specified current fractionalization;
computing adaptively the metric value by accumulating, from a beginning of the sorted 3D voxels, voxel metric effects representing volumes of the sorted 3D voxels each weighted by the weight factor of their respective regions, where the respective weight factors are signed scalars;
identifying, from the sorted 3D voxels, a terminal voxel having a corresponding current threshold, the inclusion of the weighted volume of the terminal voxel resulting in a decrease of the adaptively generated metric value exceeding a specified tolerance; and
determining, for the stimulation location, the first metric value to be the adaptively generated metric value, and the first stimulation current based on the terminal current threshold.

19. The method of claim 17, further comprising:
generating amplitude bins of non-overlapping amplitude ranges sorted in an ascending order;
categorizing each of the 3D voxels into one of the amplitude bins based on voxel current thresholds associated with the 3D voxels;
computing, for each of the amplitude bins that includes a set of the categorized 3D voxels, a respective amplitude effect using a sum of voxel metric effect of the set of the categorized 3D voxels, the voxel metric effect representing a volume of a categorized 3D voxel weighted by a corresponding weight factor;
computing adaptively a metric value by accumulating, from a beginning of the ordered amplitude bins, the amplitude effects of the ordered amplitude bins; and
identifying, from the ordered amplitude bins, a terminal amplitude bin associated with a terminal amplitude range, the inclusion of an amplitude effect of the terminal amplitude bin resulting in a decrease of the adaptively generated metric value exceeding a specified tolerance; and
determining, for the stimulation location, the first metric value to be the generated metric value, and the first stimulation current based on the terminal amplitude range.

20. The method of claim 14, further comprising:
generating one or more virtual electrode steering parameters for steering a virtual electrode on a graphical user interface;
constructing a virtual electrode field model comprising a plurality of electrode primitives each having respective primitive voltage fields;
constructing a voltage field of the virtual electrode using superposition of the primitive voltage fields of the plurality of electrode primitives each scaled by respective weight factors; and
converting the voltage field of the virtual electrode to a voltage field of the plurality of electrodes using regression fitting.

* * * * *